US007255988B2

(12) United States Patent
Halle et al.

(10) Patent No.: US 7,255,988 B2
(45) Date of Patent: Aug. 14, 2007

(54) USE OF α 1-ANTICHYMOTRYPSIN POLYPEPTIDES, OR NUCLEIC ACIDS ENCODING THEM, OR OF A CELL WHICH IS EXPRESSING AN ACT POLYPEPTIDE, OR A NUCLEIC ACID ENCODING IT, FOR TREATMENT AND/OR PREVENTION OF DIABETES-ASSOCIATED AND/OR ARTERIAL POORLY HEALING WOUNDS AND FOR IDENTIFYING PHARMACOLOGICALLY ACTIVE SUBSTANCES

(75) Inventors: Jörn-Peter Halle, Penzberg (DE); Andreas Goppelt, München (DE); Peter Hof, Martinsried (DE)

(73) Assignee: Switch Biotech AG, Neuried (DE)

( * ) Notice: Subject to any disclaimer, the term of this patent is extended or adjusted under 35 U.S.C. 154(b) by 589 days.

(21) Appl. No.: 10/135,629

(22) Filed: Apr. 30, 2002

(65) Prior Publication Data

US 2003/0073657 A1 Apr. 17, 2003

Related U.S. Application Data

(60) Provisional application No. 60/323,348, filed on Sep. 18, 2001.

(30) Foreign Application Priority Data

Apr. 30, 2001 (DE) ................................ 10121255

(51) Int. Cl.
*G01N 31/00* (2006.01)

(52) U.S. Cl. ........................................................ 435/6

(58) Field of Classification Search .................... 435/6; 514/44; 424/9.1
See application file for complete search history.

(56) References Cited

U.S. PATENT DOCUMENTS 5,367,064 A 11/1994 Rubin et al.

FOREIGN PATENT DOCUMENTS

| | | | |
|---|---|---|---|
| EP | 0 162 812 | B1 | 11/1985 |
| EP | 0 432 117 | B1 | 6/1991 |
| EP | 1 114 862 | A2 | 7/2001 |
| WO | WO95/27053 | | 10/1995 |
| WO | WO95/27055 | | 10/1995 |

OTHER PUBLICATIONS

Witkowski et al. Biochemistry (1999) vol. 38, pp. 11643-11650.*

Seffernick et al. Journal of Bacteriology (2001) vol. 183(8), pp. 2405-2410.*

Chandra et al., "Sequence Homology Between Human α1-Antichymotrypsin, α1-Antitrypsin, and Antithrombin III," *Biochemistry* 22:5055:5060 (1983).

Dobschuetz et al., "Inhibition of Neutrophil Proteinases by Recombinant Serpin Lex032 Reduces Capillary No-Reflow in Ischemia/Reperfusion-Induced Acute Pancreatitis," *The Journal of Pharmacology and Experimental Therapeutics* 290:782-788 (1999).

Eriksson et al., "Familial $\alpha_1$-Antichymotrypsin Deficiency," *Acta Med Scand* 220:447-453 (1986).

Glinski et al., "Decreased Specific Anti-Elastase Activity in the Uninvolved Skin of Patients with Psoriasis," *Arch Dermatol Res* 283:224-229 (1991).

Harvima et al., "Decreased Chymase Activity is Associated with Increased Levels of Protease Inhibitors in Mast Cells of Psoriatic Lesions," *Acta Derm Venereol* 79:98-104 (1999).

Inglis et al., "Isolation of Two cDNAs Encoding Novel $\alpha_1$-Antichymotrypsin-Like Proteins in a Murine Chondrocytic Cell Line," *Gene* 106:213-220 (1991).

Kalsheker et al., "$\alpha_1$-Antichymotrypsin" *Int. J. Biochem. Cell Biol.* 28:961-964 (1996).

Kelly et al., "The Assessment of Antichymotrypsin in Cancer Monitoring," *Biomedicine* 28:209-215 (1978).

Lindmark et al., "Heterozygous $\alpha_1$-Antichymotrypsin Deficiency May be Associated with Cold Urticaria," *Allergy* 47:456-458 (1992).

Morii et al., "Amino Acid Sequence at the Reactive Site of Human $\alpha_1$-Antichymotrypsin," *The Journal of Biological Chemistry* 258:12749-12752 (1988).

Rubin et al., "Conversion of $\alpha_1$-Antichymotrypsin Into a Human Neutrophil Elastase Inhibitor: Demonstration of Variants with Different Association Rate Constants, Stoichiometries of Inhibition, and Complex Stabilities," *Biochemistry* 33:7627-7633 (1994).

Schick et al., "Squamous Cell Carcinoma Antigen 2 is a Novel Serpin that Inhibits the Chymotrypsin-Like Proteinases Cathepsin G and Mast Cell Chymase," *The Journal of Biological Chemistry* 272:1849-1855 (1997).

Tegner et al., "Quantitation of Human Granulocyte Protease Inhibitors in Non-Purulent Bronchial Lavage Fluids," *Acta Otolaryngol* 85:282-289 (1978).

Travis et al., "Human α-1-Antichymotrypsin: Interaction with Chymotrypsin-Like Proteinases," *Biochemistry* 17:5651-5656 (1978).

* cited by examiner

*Primary Examiner*—Jon Angell
(74) *Attorney, Agent, or Firm*—Clark & Elbing LLP

(57) ABSTRACT

The invention relates to the use of alpha 1-antichymotrypsin (ACT) polypeptides according to SEQ ID No. 1 to SEQ ID No. 4 and/or nucleic acids encoding them, or an antibody or a fragment thereof directed against the polypeptide, or of a cell which is expressing the polypeptide or a nucleic acid encoding it, for diagnosis, treatment and/or prevention of diabetes-associated and/or arterial wounds which heal poorly and for identifying pharmacologically active substances which exert an influence on the expression or function, particularly the activity of ACT.

4 Claims, No Drawings

SEQUENCE LISTING

<160> NUMBER OF SEQ ID NOS: 18

<210> SEQ ID NO 1
<211> LENGTH: 418
<212> TYPE: PRT
<213> ORGANISM: Mus musculus

<400> SEQUENCE: 1

```
Met Ala Phe Ile Ala Ala Leu Gly Leu Leu Met Ala Arg Ile Cys Pro
 1               5                  10                  15

Ala Val Leu Ser Phe Pro Asp Gly Thr Leu Gly Met Asp Ala Ala Val
            20                  25                  30

Gln Glu Asp His Asp Asn Gly Thr Gln Leu Asp Ser Leu Thr Leu Ala
        35                  40                  45

Ser Ile Asn Thr Asp Phe Ala Phe Ser Leu Tyr Lys Glu Leu Val Leu
    50                  55                  60

Lys Asn Pro Asp Thr Asn Ile Val Phe Ser Pro Leu Ser Ile Ser Ala
65                  70                  75                  80

Ala Leu Ala Leu Val Ser Leu Gly Ala Lys Gly Asn Thr Leu Glu Glu
                85                  90                  95

Ile Leu Glu Gly Leu Lys Phe Asn Leu Thr Glu Thr Ser Glu Ala Asp
            100                 105                 110

Ile His Gln Gly Phe Gly His Leu Leu Gln Arg Leu Asn Gln Pro Lys
        115                 120                 125

Asp Gln Val Gln Ile Ser Thr Gly Ser Ala Leu Phe Ile Glu Lys Arg
    130                 135                 140

Gln Gln Ile Leu Thr Glu Phe Gln Glu Lys Ala Lys Thr Leu Tyr Gln
145                 150                 155                 160

Ala Glu Ala Phe Thr Ala Asp Phe Gln Gln Pro Arg Gln Ala Lys Lys
                165                 170                 175

Leu Ile Asn Asp Tyr Val Arg Lys Gln Thr Gln Gly Met Ile Lys Glu
            180                 185                 190

Leu Val Ser Asp Leu Asp Lys Arg Thr Leu Met Val Leu Val Asn Tyr
        195                 200                 205

Ile Tyr Phe Lys Ala Lys Trp Lys Val Pro Phe Asp Pro Leu Asp Thr
    210                 215                 220

Phe Lys Ser Glu Phe Tyr Ala Gly Lys Arg Arg Pro Val Ile Val Pro
225                 230                 235                 240

Met Met Ser Met Glu Asp Leu Thr Thr Pro Tyr Phe Arg Asp Glu Glu
                245                 250                 255

Leu Ser Cys Thr Val Val Glu Leu Lys Tyr Thr Gly Asn Ala Ser Ala
            260                 265                 270

Leu Phe Ile Leu Pro Asp Gln Gly Arg Met Gln Gln Val Glu Ala Ser
        275                 280                 285

Leu Gln Pro Glu Thr Leu Arg Lys Trp Lys Asn Ser Leu Lys Pro Arg
    290                 295                 300

Met Ile Asp Glu Leu His Leu Pro Lys Phe Ser Ile Ser Thr Asp Tyr
305                 310                 315                 320

Ser Leu Glu Asp Val Leu Ser Lys Leu Gly Ile Arg Glu Val Phe Ser
                325                 330                 335

Thr Gln Ala Asp Leu Ser Ala Ile Thr Gly Thr Lys Asp Leu Arg Val
            340                 345                 350

Ser Gln Val Val His Lys Ala Val Leu Asp Val Ala Glu Thr Gly Thr
```

-continued

```
        355                 360                 365

Glu Ala Ala Ala Ala Thr Gly Val Lys Phe Val Pro Met Ser Ala Lys
    370                 375                 380

Leu Tyr Pro Leu Thr Val Tyr Phe Asn Arg Pro Phe Leu Ile Met Ile
385                 390                 395                 400

Phe Asp Thr Glu Thr Glu Ile Ala Pro Phe Ile Ala Lys Ile Ala Asn
                405                 410                 415

Pro Lys


<210> SEQ ID NO 2
<211> LENGTH: 418
<212> TYPE: PRT
<213> ORGANISM: Mus musculus

<400> SEQUENCE: 2

Met Ala Phe Ile Ala Ala Leu Gly Leu Leu Met Ala Gly Ile Cys Pro
 1               5                  10                  15

Ala Val Leu Cys Phe Pro Asp Gly Thr Leu Gly Met Asp Ala Ala Val
            20                  25                  30

Gln Glu Asp His Asp Asn Gly Thr Gln Leu Asp Ser Leu Thr Leu Ala
        35                  40                  45

Ser Ile Asn Thr Asp Phe Ala Phe Ser Leu Tyr Lys Glu Leu Val Leu
    50                  55                  60

Lys Asn Pro Asp Lys Asn Ile Val Phe Ser Pro Leu Ser Ile Ser Ala
65                  70                  75                  80

Ala Leu Ala Val Met Ser Leu Gly Ala Lys Gly Asn Thr Leu Glu Glu
                85                  90                  95

Ile Leu Glu Gly Leu Lys Phe Asn Leu Thr Glu Thr Ser Glu Ala Asp
            100                 105                 110

Ile His Gln Gly Phe Gly His Leu Leu Gln Arg Leu Asn Gln Pro Lys
        115                 120                 125

Asp Gln Val Gln Ile Ser Thr Gly Ser Ala Leu Phe Ile Glu Lys Arg
    130                 135                 140

Gln Gln Ile Leu Thr Glu Phe Gln Glu Lys Ala Lys Thr Leu Tyr Gln
145                 150                 155                 160

Ala Glu Ala Phe Thr Ala Asp Phe Gln Gln Pro Arg Gln Ala Lys Lys
                165                 170                 175

Leu Ile Asn Asp Tyr Val Arg Lys Gln Thr Gln Gly Met Ile Lys Glu
            180                 185                 190

Leu Val Ser Asp Leu Asp Lys Arg Thr Leu Met Val Leu Val Asn Tyr
        195                 200                 205

Ile Tyr Phe Lys Ala Lys Trp Lys Val Pro Phe Asp Pro Leu Asp Thr
    210                 215                 220

Phe Lys Ser Glu Phe Tyr Cys Gly Lys Arg Arg Pro Val Ile Val Pro
225                 230                 235                 240

Met Met Ser Met Glu Asp Leu Thr Thr Pro Tyr Phe Arg Asp Glu Glu
                245                 250                 255

Leu Ser Cys Thr Val Val Glu Leu Lys Tyr Thr Gly Asn Ala Ser Ala
            260                 265                 270

Leu Phe Ile Leu Pro Asp Gln Gly Arg Met Gln Gln Val Glu Ala Ser
        275                 280                 285

Leu Gln Pro Glu Thr Leu Arg Lys Trp Lys Asn Ser Leu Lys Pro Arg
    290                 295                 300

Met Ile Asp Glu Leu His Leu Pro Lys Phe Ser Ile Ser Thr Asp Tyr
```

-continued 305 310 315 320

Ser Leu Glu Asp Val Leu Ser Lys Leu Gly Ile Arg Glu Val Phe Ser
325 330 335

Thr Gln Ala Asp Leu Ser Ala Ile Thr Gly Thr Lys Asp Leu Arg Val
340 345 350

Ser Gln Val Val His Lys Ala Val Leu Asp Val Ala Glu Thr Gly Thr
355 360 365

Glu Ala Ala Ala Ala Thr Gly Val Lys Phe Val Pro Met Ser Ala Lys
370 375 380

Leu Tyr Pro Leu Thr Val Tyr Phe Asn Arg Pro Phe Leu Ile Met Ile
385 390 395 400

Phe Asp Thr Glu Thr Glu Ile Ala Pro Phe Ile Ala Lys Ile Ala Asn
405 410 415

Pro Lys

<210> SEQ ID NO 3
<211> LENGTH: 423
<212> TYPE: PRT
<213> ORGANISM: Homo sapiens

<400> SEQUENCE: 3

Met Glu Arg Met Leu Pro Leu Leu Thr Leu Gly Leu Leu Ala Ala Gly
1 5 10 15

Phe Cys Pro Ala Val Leu Cys His Pro Asn Ser Pro Leu Asp Glu Glu
20 25 30

Asn Leu Thr Gln Glu Asn Gln Asp Arg Gly Thr His Val Asp Leu Gly
35 40 45

Leu Ala Ser Ala Asn Val Asp Phe Ala Phe Ser Leu Tyr Lys Gln Leu
50 55 60

Val Leu Lys Ala Pro Asp Lys Asn Val Ile Phe Ser Pro Leu Ser Ile
65 70 75 80

Ser Thr Ala Leu Ala Phe Leu Ser Leu Gly Ala His Asn Thr Thr Leu
85 90 95

Thr Glu Ile Leu Lys Gly Leu Lys Phe Asn Leu Thr Glu Thr Ser Glu
100 105 110

Ala Glu Ile His Gln Ser Phe Gln His Leu Leu Arg Thr Leu Asn Gln
115 120 125

Ser Ser Asp Glu Leu Gln Leu Ser Met Gly Asn Ala Met Phe Val Lys
130 135 140

Glu Gln Leu Ser Leu Leu Asp Arg Phe Thr Glu Asp Ala Lys Arg Leu
145 150 155 160

Tyr Gly Ser Glu Ala Phe Ala Thr Asp Phe Gln Asp Ser Ala Ala Ala
165 170 175

Lys Lys Leu Ile Asn Asp Tyr Val Lys Asn Gly Thr Arg Gly Lys Ile
180 185 190

Thr Asp Leu Ile Lys Asp Leu Asp Ser Gln Thr Met Met Val Leu Val
195 200 205

Asn Tyr Ile Phe Phe Lys Ala Lys Trp Glu Met Pro Phe Asp Pro Gln
210 215 220

Asp Thr His Gln Ser Arg Phe Tyr Leu Ser Lys Lys Lys Trp Val Met
225 230 235 240

Val Pro Met Met Ser Leu His His Leu Thr Ile Pro Tyr Phe Arg Asp
245 250 255

Glu Glu Leu Ser Cys Thr Val Val Glu Leu Lys Tyr Thr Gly Asn Ala

-continued

```
            260                 265                 270

Ser Ala Leu Phe Ile Leu Pro Asp Gln Asp Lys Met Glu Glu Val Glu
        275                 280                 285

Ala Met Leu Leu Pro Glu Thr Leu Lys Arg Trp Arg Asp Ser Leu Glu
    290                 295                 300

Phe Arg Glu Ile Gly Glu Leu Tyr Leu Pro Lys Phe Ser Ile Ser Arg
305                 310                 315                 320

Asp Tyr Asn Leu Asn Asp Ile Leu Leu Gln Leu Gly Ile Glu Glu Ala
                325                 330                 335

Phe Thr Ser Lys Ala Asp Leu Ser Gly Ile Thr Gly Ala Arg Asn Leu
            340                 345                 350

Ala Val Ser Gln Val Val His Lys Ala Val Leu Asp Val Phe Glu Glu
        355                 360                 365

Gly Thr Glu Ala Ser Ala Ala Thr Ala Val Lys Ile Thr Leu Leu Ser
    370                 375                 380

Ala Leu Val Glu Thr Arg Thr Ile Val Arg Phe Asn Arg Pro Phe Leu
385                 390                 395                 400

Met Ile Ile Val Pro Thr Asp Thr Gln Asn Ile Phe Phe Met Ser Lys
                405                 410                 415

Val Thr Asn Pro Lys Gln Ala
            420


<210> SEQ ID NO 4
<211> LENGTH: 402
<212> TYPE: PRT
<213> ORGANISM: Homo sapiens

<400> SEQUENCE: 4

Leu Cys His Pro Asn Ser Pro Leu Asp Glu Glu Asn Leu Thr Gln Glu
 1               5                  10                  15

Asn Gln Asp Arg Gly Thr His Val Asp Leu Gly Leu Ala Ser Ala Asn
            20                  25                  30

Val Asp Phe Ala Phe Ser Leu Tyr Lys Gln Leu Val Leu Lys Ala Pro
        35                  40                  45

Asp Lys Asn Val Ile Phe Ser Pro Leu Ser Ile Ser Thr Ala Leu Ala
    50                  55                  60

Phe Leu Ser Leu Gly Ala His Asn Thr Thr Leu Thr Glu Ile Leu Lys
65                  70                  75                  80

Gly Leu Lys Phe Asn Leu Thr Glu Thr Ser Glu Ala Glu Ile His Gln
                85                  90                  95

Ser Phe Gln His Leu Leu Arg Thr Leu Asn Gln Ser Ser Asp Glu Leu
            100                 105                 110

Gln Leu Ser Met Gly Asn Ala Met Phe Val Lys Glu Gln Leu Ser Leu
        115                 120                 125

Leu Asp Arg Phe Thr Glu Asp Ala Lys Arg Leu Tyr Gly Ser Glu Ala
    130                 135                 140

Phe Ala Thr Asp Phe Gln Asp Ser Ala Ala Ala Lys Lys Leu Ile Asn
145                 150                 155                 160

Asp Tyr Val Lys Asn Gly Thr Arg Gly Lys Ile Thr Asp Leu Ile Lys
                165                 170                 175

Asp Leu Asp Ser Gln Thr Met Met Val Leu Val Asn Tyr Ile Phe Phe
            180                 185                 190

Lys Ala Lys Trp Glu Met Pro Phe Asp Pro Gln Asp Thr His Gln Ser
        195                 200                 205
```

-continued

```
Arg Phe Tyr Leu Ser Lys Lys Lys Trp Val Met Val Pro Met Met Ser
    210                 215                 220

Leu His His Leu Thr Ile Pro Tyr Phe Arg Asp Glu Glu Leu Ser Cys
225                 230                 235                 240

Thr Val Val Glu Leu Lys Tyr Thr Gly Asn Ala Ser Ala Leu Phe Ile
                245                 250                 255

Leu Pro Asp Gln Asp Lys Met Glu Glu Val Glu Ala Met Leu Leu Pro
            260                 265                 270

Glu Thr Leu Lys Arg Trp Arg Asp Ser Leu Glu Phe Arg Glu Ile Gly
        275                 280                 285

Glu Leu Tyr Leu Pro Lys Phe Ser Ile Ser Arg Asp Tyr Asn Leu Asn
    290                 295                 300

Asp Ile Leu Leu Gln Leu Gly Ile Glu Glu Ala Phe Thr Ser Lys Ala
305                 310                 315                 320

Asp Leu Ser Gly Ile Thr Gly Ala Arg Asn Leu Ala Val Ser Gln Val
                325                 330                 335

Val His Lys Ala Val Leu Asp Val Phe Glu Glu Gly Thr Glu Ala Ser
            340                 345                 350

Ala Ala Thr Ala Val Lys Ile Thr Leu Leu Ser Ala Leu Val Glu Thr
        355                 360                 365

Arg Thr Ile Val Arg Phe Asn Arg Pro Phe Leu Met Ile Ile Val Pro
    370                 375                 380

Thr Asp Thr Gln Asn Ile Phe Phe Met Ser Lys Val Thr Asn Pro Lys
385                 390                 395                 400

Gln Ala
```

<210> SEQ ID NO 5
<211> LENGTH: 2035
<212> TYPE: DNA
<213> ORGANISM: Mus musculus

<400> SEQUENCE: 5

```
cacgagcaca gaggctggca gctggctggt ttcagctctg cagactgcag aacacagaag     60

atggctttca ttgcagctct ggggctcttg atggctagga tctgccctgc tgtcctctcc    120

ttcccagatg gcacgttggg aatggatgct gcagtccaag aagaccatga caatgggaca    180

caactggaca gtctcacatt ggcctccatc aacactgact ttgccttcag cctctacaag    240

gagctggttt tgaagaatcc agatacaaat attgtcttct ccccacttag catctcagcg    300

gccttggccc tcgtgtccct gggagcaaag ggcaacaccc tggaagagat tctagaaggt    360

ctcaagttca atcttacaga gacctctgag gcagacatcc accagggctt tgggcacctc    420

ctacagaggc tcaaccagcc aaaggaccag gtacagatca gcacgggtag tgccctgttt    480

attgaaaagc gccagcagat cctgacagaa ttccaggaga aggcaaagac tctgtaccag    540

gctgaggcct tcacagcaga cttccagcag cctcgacagg ccaaaaagct catcaatgac    600

tatgtgagga aacagaccca ggggatgatc aaggaactgg tctcagacct ggataaaagg    660

acattgatgg tgctggtgaa ttatatctac tttaaagcca aatggaaggt gccctttgac    720

cctcttgaca cgttcaagtc tgagttctac gcgggcaaga ggaggcccgt gatagtgccc    780

atgatgagca tggaggacct gaccacaccc tacttccgag atgaggagct gtcctgcact    840

gtggtggagc tgaagtacac aggaaatgcc agcgccctgt tcatcctccc tgaccagggc    900

aggatgcagc aggtggaagc cagcttacaa ccagagaccc tgaggaagtg gaagaattct    960

ctgaaaccca ggatgataga tgagctccac ctgcccaagt tctccatctc caccgactac   1020
```

-continued agcctggagg atgtcctttc aaagctgggc atcagggaag tcttctccac acaggctgac 1080
ctgtctgcaa tcacaggaac caaggatctg agagtctctc aggtggtcca caaggctgtg 1140
ctggatgtgg ctgagacagg cacagaagca gctgctgcca ctggagtcaa atttgtccca 1200
atgtctgcga aactgtaccc tctgactgta tatttcaatc ggcctttcct gataatgatc 1260
tttgacacag aaactgaaat tgcccccttt atagccaaga tagccaaccc caaatgagac 1320
tagaactccc caagtgttga cgcttcttcc cgggagccag gcattgagcc tgtctgtggg 1380
tctccatgtg cattttggct tccatgctct gcttggcctt ggcatgcctg gattagatag 1440
tgactaactg tgttataacc tcatgtacag acatccctgt gggaagtcag tgccgtgctc 1500
ccagacttct tggtagcact agcccatgtt cctgagcctg aaatttgtct tgtcccctac 1560
ccctgctctc tccctgtatc tgcctccacc caaaagcctg ggccccatca agtaagctca 1620
gtcccagttt agactctggt tatgtctccc ttcagccttg ctgtcttgat gggactgtgc 1680
aaccttacag gccaacccat atggaccaag aggaaagctt ggctggcccg tgtctatccg 1740
cagcatctag gactacttgg tgcccagtct gcctcactct ttcatttctc caggctttgc 1800
ctccaggcac tgcccccctg caggatctcc tcactttgtc cacatctggc acagagttag 1860
agccctcact tctgcagctg catggggtct gtgggtcaga gcagatcctt tcccctggca 1920
ctcctactta gaacaaagta gcctttcttt tagttcccag ctgaccaacc tcacacaaaa 1980
gaggaacacc aaccagaata aagaggtagg agcaaaggat caataaacat gtaac 2035

<210> SEQ ID NO 6
<211> LENGTH: 2035
<212> TYPE: DNA
<213> ORGANISM: Mus musculus

<400> SEQUENCE: 6
cacgagcaca gaggctggca gctggctggt ttcagctctg cagactgcag aacacagaag 60
atggctttca ttgcagctct ggggctcttg atggctggga tctgccctgc tgtcctctgc 120
ttcccagatg gcacgttggg aatggatgct gcagtccaag aagaccatga caatgggaca 180
caactggaca gtctcacatt ggcctccatc aacactgact ttgccttcag cctctacaag 240
gagctggttt tgaagaatcc agataaaaat attgtcttct ccccacttag catctcagcg 300
gccttggctg tcatgtccct gggagcaaag ggcaacaccc tggaagagat tctagaaggt 360
ctcaagttca atcttacaga gacctctgag gcagacatcc accagggctt tgggcacctc 420
ctacagaggc tcaaccagcc aaaggaccag gtacagatca gcacgggtag tgccctgttt 480
attgaaaagc gccagcagat cctgacagaa ttccaggaga aggcaaagac tctgtaccag 540
gctgaggcct tcacagcaga cttccagcag cctcgacagg ccaaaaagct catcaatgac 600
tatgtgagga aacagaccca ggggatgatc aaggaactgg tctcagacct ggataaaagg 660
acattgatgg tgctggtgaa ttatatctac tttaaagcca aatggaaggt gccctttgac 720
cctcttgaca cgttcaagtc tgagttctac tgcggcaaga ggaggcccgt gatagtgccc 780
atgatgagca tggaggacct gaccacaccc tacttccgag atgaggagct gtcctgcact 840
gtggtggagc tgaagtacac aggaaatgcc agcgccctgt tcatcctccc tgaccagggc 900
aggatgcagc aggtggaagc cagcttacaa ccagagaccc tgaggaagtg gaagaattct 960
ctgaaaccca ggatgataga tgagctccac ctgcccaagt tctccatctc caccgactac 1020
agcctggagg atgtcctttc aaagctgggc atcagggaag tcttctccac acaggctgac 1080

-continued

```
ctgtctgcaa tcacaggaac caaggatctg agagtgtctc aggtggtcca caaggctgtg   1140
ctggatgtgg ctgagacagg cacagaagca gctgctgcca ctggagtcaa atttgtccca   1200
atgtctgcga aactgtaccc tctgactgta tatttcaatc ggcctttcct gataatgatc   1260
tttgacacag aaactgaaat tgccccctttt atagccaaga tagccaaccc caaatgagac   1320
tagaactccc caagtgttga cgcttcttcc cgggagccag gcattgagcc tgtctgtggg   1380
tctccatgtg cattttggct tccatgctct gcttggcctt ggcatgcctg gattagatag   1440
tgactaactg tgttataacc tcatgtacag acatccctgt gggaagtcag tgccgtgctc   1500
ccagacttct tggtagcact agcccatgtt cctgagcctg aaatttgtct tgtcccctac   1560
ccctgctctc tccctgtatc tgcctccacc caaaagcctg ggccccatca agtaagctca   1620
gtcccagttt agactctggt tatgtctccc ttcagccttg ctgtcttgat gggactgtgc   1680
aaccttacag gccaacccat atggaccaag aggaaagctt ggctggcccg tgtctatccg   1740
cagcatctag gactacttgg tgcccagtct gcctcactct ttcatttctc caggctttgc   1800
ctccaggcac tgccccccctg caggatctcc tcactttgtc cacatctggc acagagttag   1860
agccctcact tctgcagctg catggggtct gtgggtcaga gcagatcctt tcccctggca   1920
ctcctactta gaacaaagta gcctttcttt tagttcccag ctgaccaacc tcacacaaaa   1980
gaggaacacc aaccagaata aagaggtagg agcaaaggat caataaacat gtaac        2035
```

<210> SEQ ID NO 7
<211> LENGTH: 1522
<212> TYPE: DNA
<213> ORGANISM: Homo sapiens

<400> SEQUENCE: 7

```
cagagttgag aatggagaga atgttacctc tcctgactct ggggctcttg gcggctgggt     60
tctgccctgc tgtcctctgc caccctaaca gcccacttga cgaggagaat ctgacccagg    120
agaaccaaga ccgagggaca cacgtggacc tcggattagc ctccgccaac gtggacttcg    180
ctttcagcct gtacaagcag ttagtcctga aggcccctga taagaatgtc atcttctccc    240
cactgagcat ctccaccgcc ttggccttcc tgtctctggg ggcccataat accaccctga    300
cagagattct caaaggcctc aagttcaacc tcacggagac ttctgaggca gaaattcacc    360
agagcttcca gcacctcctg cgcaccctca atcagtccag cgatgagctg cagctgagta    420
tgggaaatgc catgtttgtc aaagagcaac tcagtctgct ggacaggttc acggaggatg    480
ccaagaggct gtatggctcc gaggcctttg ccactgactt tcaggactca gctgcagcta    540
agaagctcat caacgactac gtgaagaatg gaactagggg gaaaatcaca gatctgatca    600
aggaccttga ctcgcagaca atgatggtcc tggtgaatta catcttcttt aaagccaaat    660
gggagatgcc ctttgacccc caagatactc atcagtcaag gttctacttg agcaagaaaa    720
agtgggtaat ggtgcccatg atgagtttgc atcacctgac tataccttac ttccgggacg    780
aggagctgtc ctgcaccgtg gtggagctga agtacacagg caatgccagc gcactcttca    840
tcctccctga tcaagacaag atggaggaag tggaagccat gctgctccca gagaccctga    900
agcggtggag agactctctg gagttcagag agataggtga gctctacctg ccaaagtttt    960
ccatctcgag ggactataac ctgaacgaca tacttctcca gctgggcatt gaggaagcct   1020
tcaccagcaa ggctgacctg tcagggatca caggggccag gaacctagca gtctcccagg   1080
tggtccataa ggctgtgctt gatgtatttg aggagggcac agaagcatct gctgccacag   1140
cagtcaaaat caccctcctt tctgcattag tggagacaag gaccattgtg cgtttcaaca   1200
```

-continued

```
ggcccttcct gatgatcatt gtccctacag acacccagaa catcttcttc atgagcaaag   1260

tcaccaatcc caagcaagcc tagagcttgc catcaagcag tggggctctc agtaaggaac   1320

ttggaatgca agctggatgc ctgggtctct gggcacagcc tggcccctgt gcaccgagtg   1380

gccatggcat gtgtggccct gtctgcttat ccttggaagg tgacagcgat tccctgtgaa   1440

gctctcacac gcacaggggc ccatggactc ttcagtctgg agggtcctgg cctcctgaca   1500

gcaataaata atttcgttgg cc                                            1522
```

<210> SEQ ID NO 8
<211> LENGTH: 1428
<212> TYPE: DNA
<213> ORGANISM: Homo sapiens

<400> SEQUENCE: 8

```
ctctgccacc ctaacagccc acttgacgag gagaatctga cccaggagaa ccaagaccga     60

gggacacacg tggacctcgg attagcctcc gccaacgtgg acttcgcttt cagcctgtac    120

aagcagttag tcctgaaggc ccctgataag aatgtcatct tctccccact gagcatctcc    180

accgccttgg ccttcctgtc tctgggggcc cataatacca ccctgacaga gattctcaaa    240

ggcctcaagt tcaacctcac ggagacttct gaggcagaaa ttcaccagag cttccagcac    300

ctcctgcgca ccctcaatca gtccagcgat gagctgcagc tgagtatggg aaatgccatg    360

tttgtcaaag agcaactcag tctgctggac aggttcacgg aggatgccaa gaggctgtat    420

ggctccgagg cctttgccac tgactttcag gactcagctg cagctaagaa gctcatcaac    480

gactacgtga agaatggaac tagggggaaa atcacagatc tgatcaagga ccttgactcg    540

cagacaatga tggtcctggt gaattacatc ttctttaaag ccaaatggga gatgcccttt    600

gacccccaag atactcatca gtcaaggttc tacttgagca agaaaaagtg ggtaatggtg    660

cccatgatga gtttgcatca cctgactata ccttacttcc gggacgagga gctgtcctgc    720

accgtggtgg agctgaagta cacaggcaat gccagcgcac tcttcatcct ccctgatcaa    780

gacaagatgg aggaagtgga agccatgctg ctcccagaga ccctgaagcg gtggagagac    840

tctctggagt tcagagagat aggtgagctc tacctgccaa agttttccat ctcgagggac    900

tataacctga acgacatact tctccagctg ggcattgagg aagccttcac cagcaaggct    960

gacctgtcag ggatcacagg ggccaggaac ctagcagtct cccaggtggt ccataaggct   1020

gtgcttgatg tatttgagga gggcacagaa gcatctgctg ccacagcagt caaaatcacc   1080

ctcctttctg cattagtgga gacaaggacc attgtgcgtt tcaacaggcc cttcctgatg   1140

atcattgtcc ctacagacac ccagaacatc ttcttcatga gcaaagtcac caatcccaag   1200

caagcctaga gcttgccatc aagcagtggg gctctcagta aggaacttgg aatgcaagct   1260

ggatgcctgg gtctctggca cagcctggcc cctgtgcacc gagtggccat ggcatgtgtg   1320

gccctgtctg cttatccttg gaaggtgaca gcgattccct gtgtagctct cacatgcaca   1380

ggggcccatg gactcttcag tctggagggt cctgggcctc ctggaatt                1428
```

<210> SEQ ID NO 9
<211> LENGTH: 24
<212> TYPE: DNA
<213> ORGANISM: Artificial Sequence
<220> FEATURE:
<223> OTHER INFORMATION: Synthetic Primer

<400> SEQUENCE: 9

-continued gaggtaccat ggctttcatt gcag 24

<210> SEQ ID NO 10
<211> LENGTH: 35
<212> TYPE: DNA
<213> ORGANISM: Artificial Sequence
<220> FEATURE:
<223> OTHER INFORMATION: Synthetic Primer

<400> SEQUENCE: 10
gaatcacgtg accacctcct ttggggttgg ctatc 35

<210> SEQ ID NO 11
<211> LENGTH: 19
<212> TYPE: DNA
<213> ORGANISM: Mus musculus

<400> SEQUENCE: 11
atcaacggga agcccatca 19

<210> SEQ ID NO 12
<211> LENGTH: 20
<212> TYPE: DNA
<213> ORGANISM: Mus musculus

<400> SEQUENCE: 12
gacatactca gcaccggcct 20

<210> SEQ ID NO 13
<211> LENGTH: 21
<212> TYPE: DNA
<213> ORGANISM: Mus musculus

<400> SEQUENCE: 13
tccagttgtg tcccattgtc a 21

<210> SEQ ID NO 14
<211> LENGTH: 21
<212> TYPE: DNA
<213> ORGANISM: Mus musculus

<400> SEQUENCE: 14
ctgtcctctg cttcccagat g 21

<210> SEQ ID NO 15
<211> LENGTH: 21
<212> TYPE: DNA
<213> ORGANISM: Homo sapiens

<400> SEQUENCE: 15
aggcctttgc cactgacttt c 21

<210> SEQ ID NO 16
<211> LENGTH: 21
<212> TYPE: DNA
<213> ORGANISM: Homo sapiens

<400> SEQUENCE: 16
gcgagtcaag gtccttgatc a 21

<210> SEQ ID NO 17
<211> LENGTH: 20
<212> TYPE: DNA
<213> ORGANISM: Mus musculus -continued

```
<400> SEQUENCE: 17

ggaatggcaa gaccagcaag                                              20


<210> SEQ ID NO 18
<211> LENGTH: 20
<212> TYPE: DNA
<213> ORGANISM: Mus musculus

<400> SEQUENCE: 18

ggatactgcg agcaaatggg                                              20
```

USE OF α 1-ANTICHYMOTRYPSIN POLYPEPTIDES, OR NUCLEIC ACIDS ENCODING THEM, OR OF A CELL WHICH IS EXPRESSING AN ACT POLYPEPTIDE, OR A NUCLEIC ACID ENCODING IT, FOR TREATMENT AND/OR PREVENTION OF DIABETES-ASSOCIATED AND/OR ARTERIAL POORLY HEALING WOUNDS AND FOR IDENTIFYING PHARMACOLOGICALLY ACTIVE SUBSTANCES

This invention claims priority under 35 U.S.C. § 119(e) from U.S. Provisional Application Ser. No. 60/323,348, filed Sep. 18, 2001 and claims the benefit of German Patent Application Serial No. 10121255.0, filed Apr. 30, 2001.

The invention relates to the use of alpha 1-antichymotrypsin (ACT) polypeptides and/or nucleic acids encoding them, or of a cell which is expressing an ACT polypeptide or a nucleic acid encoding it, for diagnosis, treatment and/or prevention poorly healing diabetes-associated and/or poorly healing arterial wounds and for identifying pharmacologically active substances which exert an effect on the expression or function of ACT.

Skin wounds in healthy patients normally heal without any complications. However, a large number of temporal and spatial changes in the cell composition of the skin is required in order to achieve complete healing of the tissue. This process can last up to 2 years and is always associated with scar formation in non-fetal tissue. This points to the enormous complexity of the wound healing process in the skin. During the wound healing process, it is possible to distinguish different temporal and partially overlapping phases: coagulation, inflammation, proliferation and remodeling (The Physiology of Wound Healing, 1998, Oxford Institute for Continuing Education). During coagulation, blood platelets aggregate and release growth and coagulation factors. A fibrin matrix is formed, thus enabling cells to migrate into the wound. Approximately 5–7 days after injury, an inflammatory reaction is triggered by the migration of a variety of cell types into the wound, in particular neutrophilic granulocytes and monocytes which release the mediators of the inflammatory reaction. During the proliferation phase blood vessels are restored, damaged tissue is regenerated, and the regenerated tissue is remodeled. The processes during the proliferation phase comprise, in particular, neovascularization, fibroblast proliferation and reepithelialization due to the proliferation and differentiation of keratinocytes. The fibroblasts secrete several growth factors, such as PDGF and TGF-beta, which in turn regulate the synthesis and deposition of components of the extracellular matrix (ECM), such as fibronectin, laminin, glycosaminoglycans and collagen. During the reorganization of the tissue, the ECM components, particularly collagene, are rearranged. As a result of collagene being continuously degraded and newly synthesized, the reepithelialized wound can mature, and a flat scar is formed within 2 years. Again, a large number of growth factors and chemoattractants are required for reconstructing the tissue in a coordinated manner. Thus, interleukin 1, TNF-beta and interferon-gamma influence the secretion of the ECM components. TGF-beta, PDGF and FGF are also essential for remodeling.

However, in addition to the processes which contribute to the reconstruction of destroyed structures, proteolytic processes are also important for wound healing. Proteolytic processes participate in the removal of cell debris and the degradation of intermediate structures, such as fibrin matrix.

Thus, a large number of proteases are active at the edge of the wound (Martin et al., 1997, Science, 276: 75–81). For example, plasminogen is activated by plasminogen activator and the urokinase-type plasminogen activator is upregulated in migrating keratinocytes, enabling them to degrade the fibrin matrix located ahead of them. This is consistent with the observation that plasminogen-knock-out mice exhibit virtually no reepithelialization. Metalloproteinases (MMP) also play an important role. MMP9 (gelatinase B), MMP1 (interstitial collagenase) and MMP10 (stromelysin-2) are activated at various time points and are characterized by different substrate specificities. Neutrophilic granulocytes and monocytes (macrophages) also secrete proteases (Dome et al., 1999, Wound Rep. Reg. 7: 433–441; Shapiro et al., J. Rheumatol. Suppl., 1991, 27; 95–98). Monocytes contain the intracellular serine proteases elastase and cathepsin G and secrete small amounts of metalloproteinases. On the other hand, in differentiating mononuclear phagocytes, the expression of cathepsin G is suppressed and the expression of collagenase is delayed. It has been observed that, in mature macrophages, the expression of metalloproteinases is powerfully induced following stimulation (Shapiro et al., J. Rheumatol. Suppl., 1991, 27: 95–98).

With regard to chronic wounds, it is the matrix metalloproteinases which have become the focus of particular interest. Thus, the amounts of collagenolytic activity which are found in the exudates of chronic wounds are significantly increased compared to those found in the exudates of surgical wounds or open skin wounds (Yager et al., 1996, J. Invest. Dermatol. 107: 743–748).

For example, a variety of investigations provide evidence that the amount of MMP-1 is markedly increased in chronic wounds and that MMP-1 is the predominant collagenase in the exudates of chronic wounds (Vaalamo et al., 1997, J. Invest. Dermatol., 109; 96–101; Nwomeh et al., 1999. J. Surg. Res., 81; 189–195). MMP8 is also expressed more strongly in chronic wounds (Yager et al., 1996, J. Invest. Dermatol. 107: 743–748; Nwomeh et al., 1999, J. Surg. Res., 81: 189–195). In addition to the MMPs belonging to the interstitial collagenase class, other MMPs, namely the gelatinases MMP2 and MMP9 and the stromelysins MMP3, MMP 10 and MMP11, have been demonstrated to be present in increased amounts in chronic wounds (Nagase and Woessner, 1999, J. Biol. Chem., 274; 21491–21494). It has been postulated that serine protease activity, namely elastase activity, is present in chronic wounds, with this activity degrading fibrin and fibronectin (Palolahti et al., 1993, Exp. Dermatol., 2: 29–37; Rao et al., 1995, J. Invest. Dermatol., 105; 572–578; Grinnell and Zhu, 1996, J. Invest. Dermatol., 106: 335–341; Herrick et al., 1997, Lab. Invest. 77: 281–288).

Another serine protease, cathepsin G, has been detected in the granulation tissue in chronic decubitus ulcers (Rogers et al., 1995; Wound Rep. Reg., 3: 273–283). In contrast, it was not possible to observe any increased amounts of cathepsin G in venous foot ulcers (Weckroth et al., 1996, J. Invest. Dermatol., 106: 1119–1124). These apparently contradicting results indicate that the term “chronic skin wounds” encompasses completely different diseases with differing pathogenetic backgrounds. In general, diabetic ulcers, venous ulcers, arterial ulcers and decubitus ulcers are discriminated. Decubitus ulcers are very deep wounds which are accompanied by necrosis, infection and maceration of the tissue. They are formed due to prolonged pressure to a given skin area. By contrast, venous ulcers are rather superficial and are caused by venous stasis whereas arterial ulcers are frequently caused by arterial occlusion diseases. Diabetic ulcers, in turn, are ulcers which often arise in diabetic patients. Among a large number of diabetes-associated complications, the late complications of diabetes also comprise characteristic changes in the skin such as frequent infections, trophic disturbances and *necrobiosis lipoidica*. These changes can develop into poorly healing ulcers, frequently as the result of microangiopathic disturbances. The epidemiological importance of these diseases is clear when the following survey findings are considered: 25% of patients suffering from type II diabetes frequently develop chronic ulcers ("diabetic foot") with about half of them requiring elaborate in-patient treatment. Nevertheless these ulcers heal poorly in the end. Diabetic foot causes more hospitalization than does any other complication associated with diabetes. The number of these cases associated with diabetes type I and II is on the increase and represents approx. 2.5% of all hospital admissions.

It has been postulated that a disturbed, excessively powerful proteolytic activity is responsible for the poor healing in chronic wounds (Yager et al., 1999, Wound Rep. Reg., 7: 433–441). In normally healing wounds, an equilibrium between proteolytic and antiproteolytic activity is brought about by a broad range of protease inhibitors. This theory is supported by the observation of reduced amounts of protease inhibitors within chronic wounds such as the metalloproteinase inhibitor TIMP-1, the nonspecific protease inhibitor alpha2-macroglobulin and the elastase inhibitor alpha1-protease inhibitor (Yager et al., 1997, Wound Rep. Reg., 5:23–32; Grinnell et al., J. Invest. Dermatol., 110; 771–776; Bullen et al., J. Invest. Dermatol., 104; 236–240; Rao et al., 1995; J. Invest. Dermatol., 105: 572–578; Grinnell and Zhu, 1996, J. Invest. Dermatol., 106: 335–341). It is thought that this deficiency could lead to an incomplete "antiprotease shield" with respect to those protease inhibitors. As a consequence, the turnover rate of collagene is faster than its synthesis. These results are confirmed by other studies (Nwomeh et al., 1999, J. Invest. Dermatol., 81: 189–195; Vaalamo et al., 1996, Br. J. Dermatol., 135; 52–59; Witte et al., 1998, Surgery 124: 464–470). It has therefore been suggested to increase the antiprotease shield by raising or inducing the expression of the protease inhibitors which are reduced or lacking, respectively, by administering exogenous protease inhibitors. A large number of inhibitors of the metalloproteinases have been developed on the basis of this hypothesis (e.g. WO200073295; U.S. Pat. No. 6,166,084; WO200105397; WO200063165; WO200046189; WO200044723; DE19851184; U.S. Pat. No. 6,071,903; EP-1004578; EP-949246; WO9858925; EP-878467); none of which has, however, been authorized as a pharmaceutical which is intended for treatment chronic skin wounds and which intervenes in the protease-antiprotease equilibrium. Furthermore, research to date did not discriminate between the various diseases which are grouped under the term "chronic ulcers". For this reason, the results of the studies cannot readily be transferred to other disturbances within the wound healing process. Thus up until now, there have been no effective therapies for chronic wound healing disturbances. Established forms of therapy are restricted to physical support of the wound healing (e.g. dressings, compresses and gels), to the scraping out of necrotic tissue and to the transplantation of skin tissues, cultured skin cells and/or matrix proteins. In recent years, growth factors have been tested for their ability to improve wound healing without, however, being able to improve the conventional therapy in a decisive manner.

In view of the strongly increasing number of diabetes II patients world-wide, and the large number of patients who are suffering from arterial ulcers, there is a large demand for novel active compounds which crucially improve the healing of poorly healing diabetes-associated and poorly healing arterial wounds. Therefore, the object of the present invention was to find a novel active compound which crucially improves the healing of poorly healing diabetes-associated and poorly healing arterial wounds.

Surprisingly, the present invention shows that the expression of murine ACT in the wounds of diabetic mice turned out to be significantly decreased as compared with that in intact skin, while a marked increase in ACT expression, as compared with that in intact skin, was observed both in the wounds of normally healing control animals and in the poorly healing wounds of old animals and in dexamethasone-treated animals suffering from poor wound healing. In comparison to the wound healing process in healthy subjects, a strongly reduced capability for up-regulation of the level of expression of ACT was also demonstrated for chronic, diabetic ulcera in human. This points to specific deregulation of ACT expression in the case of the poorly healing wounds of diabetic mammals and of diabetic humans as well as in poorly healing arterial wounds. In normally healing control animals and in healthy humans, the expression of ACT increases drastically in the wound tissue following wounding. A further experiment established that besides the reduced levels of ACT transcripts, the activity of the ACT polypeptides is also selectively decreased in poorly-healing diabetic wounds compared to the oberserved increase in activity in normally healing wounds as well as in venous ulcers. Thus, it is the increase of both expression and function, particularly the activity, which leads to a strengthening of the antiprotease shield, and which in turn allows an increased neosynthesis of collagene and consequently supports rapid wound healing in normally healing wounds. The surprising observation that both the strength of the expression and the function, particularly the activity, of ACT in the case of the poorly healing wounds of diabetic mammals and in diabetic humans one hand and of poorly healing arterial wounds on the other hand did not change or was strongly reduced relative to that in intact skin or relative to normal wound healing, respectively, opened the possibility for a treatment of wound healing by increasing the amount and the function, particularly the activity of ACT in the wound. Furthermore, the results show that this disturbance in the ACT protease inhibitor equilibrium is specific for the poorly healing wounds of diabetic mammals and diabetic humans as well as for poorly healing arterial wounds. In the case of the wound healing disturbances seen in the poorly healing wounds of old animals and in the dexamethazone-treated animals suffering from poor wound healing, other factors have to be considered as being responsible for the poor wound healing since, in these cases, there was no aberrant regulation of ACT expression and function, particularly the activity, in wounds as compared with intact skin or normal wound healing, respectively.

The experiments (e.g. Example 3) which were carried out within the context of this invention demonstrate the efficacy of the use, according to the invention, of ACT polypeptides for treatment of poorly healing wounds of diabetic mammals and poorly healing arterial wounds. It was possible to achieve a pronounced improvement of wound healing of the poorly healing wounds of diabetic animals by increasing the murine ACT homologue (mACT) in the wounds of diabetic rats with arterial impairment versus normally healing wounds, whereas the wound healing of normally healing wounds was not affected by administering mACT. The decreased expression of the ACT is causally involved in poor wound healing, specifically for poorly healing diabetes-associated and poorly healing arterial wounds. The problem is therefore solved by the use of at least one ACT polypeptide according to SEQ ID No. 1 to SEQ ID No. 4, or functional variants thereof, or nucleic acids encoding them, or variants thereof, or of a cell which is expressing an ACT polypeptide according to SEQ ID No. 1 to SEQ ID No. 4, or a nucleic acid encoding it, for treatment and/or prevention diabetes-associated and/or arterial poorly healing wounds in mammals.

The object of the invention is solved by the embodiments described in the claims. The claims are incorporated herein by reference.

ACT is known to be one of two known endogenous protease inhibitors of cathepsin G, with ACT differing from the other protease inhibitor, SCCA2 (squamous cell carcinoma antigen 2), by the fact that it specifically inhibits cathepsin G and does not exert any measurable effect on elastase (Travis et al., 1978, Biochemistry, 17; 5651–5656; Schick et al., 1997, J. Biol. Chem., 272: 1849–1855), whereas the other protease inhibitor, SCCA2, inhibits both cathepsin G and elastase. In humans, one ACT gene is known, with polymorphism having been described, particularly in the signal peptide sequence (Rubin, 1989, database entry). An allele identified in this study and the sequence of a polypeptide fragment containing the mature protein and 4 amino acids of the signal peptide (U.S. Pat. No. 5,367,064-A), are listed in SEQ ID No. 3 and SEQ ID No. 4, respectively, while the corresponding cDNAs are listed under SEQ ID No. 7 and SEQ ID No. 8 of the sequence listing. In the case of rodents, there is evidence for a large number of genes which are homologous to ACT, with the mouse serine protease inhibitor 2-2 (SEQ ID No. 2; trEMBL: Q62258) being the functional homologue to the human ACT gene since extensive concordance exists with regard to the reactive center, the tissue distribution and the inducibility following inflammation (Inglis et al., 1991, Gene 106: 213–220). Other members of the rodent serine protease inhibitor 2-2 family are spi2-2 and spi3 in the rat and an spi2-2 homologue from Adodemus sylvaticus (Inglis et al., see above). The reactive center is essential for the protease inhibitor specificity (Rubin et al., Biochemistry, 33: 7627–7633), with amino acids 356–361 of the mature protein without signal peptide being particularly crucial for the specificity. Amino acid 358 of the mature protein without signal peptide, corresponding to what is termed position P1, appears to be of particular importance in this respect since a mutation in this amino acid leads to measurable, even if only weak, elastase activity. However, it is particularly those polypeptides whose reactive loop is essentially conserved, and which consequently do not exhibit any inhibitory effect on elastase, which can be used in accordance with the invention.

The following observations provide evidence that, while ACT has been described in context with a different diseases, a link between a decrease in ACT expression and poorly healing diabetic wounds and/or poorly healing arterial wounds has never been made.

Inherited ACT deficiency is pleiomorphic and is frequently associated with chronic hepatitis and increased residual lung volume (Eriksson et al., 1986, Acta Med. Scand., 220, 447–453).

Furthermore, an important role in the pathogenesis of Alzheimer's disease is suggested since the neurofibrillar plaques contain a high amount of ACT (Kalsheker, 1996, Int. J. Biochem. Cell Biol., 28: 961–964). ACT nucleotide sequences are also known (Chandra et al., 1983, Biochemistry 22: 5055–5061; Morii and Travis, 1983, J. Biol. Chem., 258: 12749–12752) and a link between ACT and clinical syndromes has also been proposed and/or investigated at the level of the protein (for example Kozaka and Tazawa, 1976, Tohoku J. Exp Med 119:369–76; Kelly et al., Biomedicine 28: 209–15; Tegner, 1978; Acta Otolaryngol, 85:282–9).

ACT was also shown to inhibit chymases in mast cells, for which reason ACT has been described in the context with allergic reactions (Lindmark and Wallengren, Allergy, 1992 47:456–458). In addition, the role of the chymase and its inhibitor ACT has been investigated in psoriatic lesions. However, the results point to the chymase only playing a subordinate role in the pathomechanism of psoriasis (Harvima et al., 1999, Acta Derm. Veneorol., 79: 98–104) and the level of chymotrypsin inhibitor activity in the uninjured skin of psoriasis patients is unaltered (Glinski et al., 1991, Arch. Dermatol. Res., 283: 224–229). According to EP0432117, ACT could be used for treatment "skin inflammations", "burns", and "dermatological conditions". However, EP0432117 does not explain the meaning, of "dermatological condition". "Skin inflammation" refers to inflammatory diseases of a skin such as psoriasis or dermatitis, which is different from mechanically damaged skin, i.e. wounds, or from deterioration in the process of the restoration of the missing tissue in the course of wound healing. "Skin inflammation" therefore represents a pathological condition of the skin that does not encompass poorly healing arterial wounds or poorly healing diabetis-associated wounds according to the invention. By the same token the term "dermatological condition" does not include wounds according to the invention: the term "dermatological condition" refers to conditions of the disordered skin such as blisters, cysts, macules which represent symptoms of a disorder of the skin resulting from essentially internal processes. Wounds on the other hand are caused by mechanical forces coming from outside the body.

Taken together, although this enzyme has been known for a long time in biotechnology, and has been investigated extensively from the medical point of view, no relationship between ACT and arterial or diabetes-associated wounds which heal poorly has so far been described. Thus, no investigations exist, for example, with regard to the expression of ACT in wounds, in particular diabetes-associated or arterial wounds which heal poorly. This invention shows for the first time that among the large number of different possible wounds two poorly healing wounds, namely diabetes-associated and arterial ulcers, have unexpectedly the best chances for a successful therapy by ACT which would not have been considered by a skilled person.

The state of the art regards the treatment of wounds with protease inhibitors which specifically inhibit one protease as being unpromising and concentrates on developing protease inhibitors which inhibit more than one protease. Thus, there exist a number of mutants, inter alia of ACT, which act on several proteases: Lex032 acts, as a combination of ACT and antitrypsin, on both cathepsin G and elastase and is used in the treatment of pancreatitis (von Dobschuetz et al., 1999, J. Pharmacol. Exp. Ther., 290: 782–8). Bifunctional mutants possessing elastase-inhibiting and cathepsin G-inhibiting properties have been disclosed for treatment of inflammatory diseases, for example chronic wounds and psoriasis (WO 95/27055). However, such hybrid mutants carry the danger of unforeseeable side-effects and interactions, whether these be with antibodies which recognize these proteins as being foreign or with other, untested proteases. By contrast, the effect on only one single protease is comparatively simple to monitor and it is therefore possible to achieve a specific curative effect with few side-effects.

In summary, therefore, the state of the art leads away from the use of ACT for treatment and/or for prevention diabetes-associated and/or arterial wounds which heal poorly and it was therefore unexpected and surprising that ACT can be used in accordance with the invention.

The invention relates to the use of an ACT polypeptide according to SEQ ID No. 1 to SEQ ID No. 4, or of a nucleic acid encoding it, or an antibody or a fragment thereof directed against a polypeptide according to SEQ ID No. 1 to SEQ ID No. 4, or a catalytic antibody directed against a polypeptide according to SEQ ID No. 1 to SEQ ID No. 4, or of a cell which is expressing an ACT polypeptide according to SEQ ID No. 1 to SEQ ID No. 4 or a nucleic acid encoding it, for diagnosis, treatment and/or prevention of diseases which are selected from poorly healing diabetes-associated wounds and/or poorly healing arterial wounds.

The term "functional variants" is to be understood as meaning variants of the polypeptides which can be used in accordance with the invention, which variants do not possess any protease inhibitor specificity with regard to capthepsin G which is significantly altered as compared with that of the native ACT polypeptide. For example, variants of said polypeptides possess at least approximately 70%, in particular at least approx. 80%, especially at least approx. 90%, sequence identity with one of the sequences SEQ ID No. 1 to SEQ ID No. 4. Functional variants of the polypeptide can also be parts of the polypeptides used in accordance with the invention which, when compared with the native ACT polypeptide, do not exhibit any significantly altered protease inhibitor specificity: for example, the first amino acid, i.e. methionine, can be missing without there being any significant change in the function of the polypeptide. N- and/or C-terminal and/or internal deletions of the polypeptide in the range of approx. 1–60, preferably of approx. 1–30, in particular of approx. 1–15, especially of approx. 1–5, amino acids are also included provided the protease inhibitor specificity remains essentially unaltered as compared with that of the native polypeptide. Particular preference is given to deletions which affect the signal peptide, or parts thereof, at the N terminus of the polypeptide. Examples of such variants, whose protease inhibitor specificity is not significantly altered as compared with that of the native polypeptide, are the polypeptides which are homologous with the polypeptides used in accordance with the invention and which are derived, in particular, from organisms other than humans or mice, preferably from non-human mammals such as monkeys, pigs and rats. Other examples of polypeptides which are encoded by different alleles of the gene, in different individuals or in different organs, and which, when compared with the native polypeptide, do not exhibit any protease inhibitor specificity which is significantly altered as compared with that of the native polypeptide in an organism. Furthermore, a posttranslational or cotranslational modification of the polypeptide chain which is present in the native state can be missing or be altered. In particular, covalently bound sugar residues can be missing or be altered.

Preferred functional variants are ACT polypeptides in which the signal peptide, or a part thereof, is deleted, for example a polypeptide according to SEQ ID No. 4. Furthermore, the ACT which can be used in accordance with the invention can be glycosylated, partially glycosylated or unglycosylated. Preference is given to human variants which have a reactive loop which is conserved in comparison to SEQ ID No. 3 and which exhibit essentially the same protease inhibitor specificity as does the mature native ACT polypeptide. Other preferred variants are serine protease inhibitor 2-2 polypeptides which like SEQ ID No. 1, contain a reactive loop which is essentially conserved.

The term "coding nucleic acid" relates to an RNA or DNA sequence which encodes an ACT polypeptide which can be used in accordance with the invention or a functional variant thereof or a precursor stage thereof, for example a pro-polypeptide or a prepropolypeptide. The polypeptide can be encoded by a full-length sequence or any part of the coding sequence as long as the polypeptide is a functional variant.

The term "variants" denotes all the DNA sequences which are complementary to a DNA sequence (reference sequence), which encode polypeptides used in accordance with the invention of the sequences SEQ ID No. 1 to SEQ ID No. 4 or their functional variants and which exhibit at least approx. 70%, in particular at least approx. 80%, especially at least approx. 90%, sequence identity with the reference sequence. The term "variants" furthermore denotes all the DNA sequences which are complementary to the reference sequence and which hybridize with the reference sequence under stringent conditions and encode a polypeptide which exhibits essentially the same activity as does the polypeptide encoded by the reference sequence, and also their degenerate forms. It is known that small changes can be present in the sequence of the nucleic acids which can be used in accordance with the invention; for example, without the property of a functional variant being lost, these changes can be brought about by the degeneracy of the genetic code or by nontranslated sequences which are appended at the 5' end and/or the 3' end of the nucleic acid. This invention therefore also encompasses so-called "variants" of the previously described nucleic acids.

The term "stringent hybridization conditions" is to be understood, in particular, as meaning those conditions in which a hybridization takes place, for example, at 60° C. in 2.5×SSC buffer, followed by several washing steps at 37° C. in a lower buffer concentration, and remains stable.

Sequence identity is understood as degree of identity (% identity) of two sequences, that in the case of polypeptides can be determined by means of for example BlastP 2.0.1 and in the case of nucleic acids by means of for example BLASTN 2.014, wherein the filter is set off and BLOSUM is 62 (Altschul et al., 1997, Nucleic Acids Res., 25:3389–3402). "Sequence homology" is understood as similarity (% positives) of two polypeptide sequences determined by means of for example BlastP 2.0.1 wherein the Filter is set off and BLOSUM is 62 (Altschul et al., 1997, Nucleic Acids Res., 25:3389–3402).

Within the meaning of the present invention, diabetes-associated wounds which heal poorly are to be understood as being skin lesions in mammals and humans suffering from diabetes. Examples of such skin lesions are to be understood as being, in particular, ulcers caused by diabetes, for example ulcus cruris arteriosum, necrobiosis lipoidica and ulcera arteriosa, and delayed wound healing which is caused by arteriosclerotic destruction of the blood vessels.

Within the meaning of the present invention the function of ACT is to be understood as the activity which ACT exerts onto protease Cathepsin G. The function of ACT also encompasses the activity of ACT in the form of complexes of ACT and Cathepsin G, i.e. the Cathepsin G:ACT complex which binds to receptors, e.g. the serpin-enzyme complex receptor (SECR) (Chen et al., 1993, Neurology 43: 1223–7; Perlmutter et al., 1990 PNAS: 87: 3753–7).

Within the meaning of the present invention, activity of ACT preferably encompasses the binding and inhibition of Cathepsin G protease. Suitable assays to determine the activity of ACT are protease inhibitory assays such as, e.g. Example 5 or Heidtmann et al., 1990, Clin Chem 36: 2077–2081.

Within the meaning of the invention, arterial wounds which heal poorly are to be understood, for example, as being ulcera arteriosa and retarded wound healing which is caused by arteriosclerotic destruction of the blood vessels.

A "reactive loop" is to be understood as being the sequence motif in an ACT polypeptide which can be used in accordance with the invention which occurs naturally, which is responsible for the specificity of the ACT polypeptide and which corresponds to amino acids 356 to 361 of the mature human ACT polypeptide, or corresponds to amino acids 360 to 365 of the human polypeptide according to SEQ ID No. 4, or corresponds to amino acids 381 to 386 of the human polypeptide according to SEQ ID No. 3, and, in the case of murine sequences, corresponds to amino acids 379–384 according to SEQ ID No. 1 or SEQ ID No. 2.

Within the meaning of the present invention, a "conserved reactive loop" is to be understood as being a reactive loop in which the only amino acid differences are those which do not lead to any significant change in protease inhibitor specificity with regard to elastase.

A "significant change in protease inhibitor specificity" with regard to elastase is to be understood as being a change which consists in an increase in elastase inhibitor activity by at least a factor of 100, in particular by at least a factor of 1000, especially by at least a factor of 10,000, as compared with the native ACT sequence or, if such an activity is not measurable in the native sequence, consists in at least a 0.0001-fold elastase inhibitor activity as compared with that of the endogenous elastase inhibitor alpha1-protease inhibitor. Assays for the determination of protease inhibitor specificity are known to the skilled person and are described below in more detail.

The nucleic acids which can be used in accordance with the invention and which encode ACT polypeptides which can be used in accordance with the invention, or their functional variants, are preferably DNA or RNA, preferably a DNA, in particular a double-stranded DNA. Furthermore, the sequence of the nucleic acids can be characterized by the fact that it possesses at least one intron and/or a polyA sequence.

In general, preference is given to a double-stranded DNA for expressing the relevant gene, both for preparing a polypeptide which can be used in accordance with the invention and in association with a vector which is applicable in gene therapy and can be used in accordance with the invention, with particular preference being given to the DNA region which encodes the polypeptide. In eukaryotes, this region begins with the first start codon (ATG) which is located in a Kozak sequence (Kozak, 1987, Nucleic. Acids Res. 15:8125–48) and extends to the next stop codon (TAG, TGA or TAA) which is located in the same reading frame as the ATG. In the case of prokaryotes, this region begins with the first AUG (or GUG) after a Shine-Dalgarno sequence and ends with the next stop codon (TAG, TGA or TAA) which is located in the same reading frame as the ATG.

Furthermore, it is possible to use a nucleic acid which has been prepared synthetically for implementing the invention. Thus, the nucleic acid which is used in accordance with the invention can, for example, be synthesized chemically, e.g. in accordance with the phosphotriester method, making use of the DNA sequences described in Table 1 and/or making use of the protein sequences which are likewise described in this table by referring to the genetic code (see, e.g., Uhlmann, E. & Peyman, A. (1990) Chemical Reviews, 90, 543–584, No. 4).

In a particularly preferred embodiment of the invention, at least one nucleic acid which can be used in accordance with the invention is contained in an expression cassette in a vector, preferably in a vector which is applicable in gene therapy. The invention also comprises the use of a vector expressing a fusion protein useable according to the invention. The vector which is applicable in gene therapy preferably contains tissue-specific, wound-specific or skin-specific, cell cycle-specific, cell type-specific, metabolism-specific or constitutively active regulatory sequences which are functionally linked to the previously described nucleic acid.

The expression vectors which are used for preparing a polypeptide which can be used in accordance with the invention can be prokaryotic or eukaryotic expression vectors. Examples of prokaryotic expression vectors are the pGEM vectors or pUC derivatives, which are used for expression in *E. coli,* and examples of eukaryotic expression vectors are the vectors p426Met25 and p426GAL1 (Mumberg et al. (1994) Nucl. Acids Res., 22, 5767–5768), which are used for expression in *Saccharomyces cerevisiae,* the Baculovirus vectors, as disclosed in EP-B1-0 127 839 or EP-B1-0 549 721, which are used for expression in insect cells, and the vectors Rc/CMV and Rc/RSV, or SV40 vectors, which are used for expression in mammalian cells, with all these vectors being generally available.

In general, the expression vectors also contain promoters which are suitable for the respective host cell, such as the trp promoter for expression in *E. coli* (see, e.g., EP-B1-0 154 133), the Met 25, GAL 1 or ADH2 promoter for expression in yeast (Russel et al. (1983), J. Biol. Chem. 258, 2674–2682; Mumberg, see above), and the baculovirus polyhedrin promoter for expression in insect cells (see 1. 13. EP-B1-0 127 839). Promoters which permit constitutive, regulable, tissue-specific, cell type-specific, cell cycle-specific or metabolism-specific expression in eukaryotic cells are suitable, for example, for expression in mammalian cells. Regulable elements in accordance with the present invention are promoters, activator sequences, enhancers, silencers and/or repressor sequences.

Examples of suitable regulable elements which permit constitutive expression in eukaryotes are promoters which are recognized by RNA polymerase III or viral promoters, CMV enhancer, CMV promoter (see also Example 3), SV40 promoter or LTR promoters, e.g. derived from MMTV (mouse mammary tumor virus; Lee et al. (1981) Nature 214, 228–232) and other viral promoter and activator sequences which are derived from, for example, HBV, HCV, HSV, HPV, EBV, HTLV or HIV.

Examples of regulable elements which permit inducible expression in eukaryotes are the tetracycline operator in combination with an appropriate repressor (Gossen M. et al. (1994) Curr. Opin. Biotechnol. 5, 516–20).

The expression of nucleic acids which can be used in accordance with the invention preferably takes place under the control of tissue-specific promoters, with skin-specific promoters, such as the human K10 promoter (Bailleul et al., 1990. Cell 62: 697–708), the human K14 promoter (Vassar et al., 1989, Proc. Natl. Acad. Sci. USA 86: 1563–67) or the bovine cytokeratin IV promoter (Fuchs et al., 1988; The Biology of Wool and Hair (eds.: G. E. Rogers, et al.), pp. 287–309. Chapman and Hall, London/New York) being particularly to be preferred.

Other examples of regulable elements which permit tissue-specific expression in eukaryotes are promoters or activator sequences from promoters or enhancers of those genes which encode proteins which are only expressed in particular cell types.

Examples of regulable elements which permit cell cycle-specific expression in eukaryotes are promoters of the following genes: cdc25A, cyclin A, cyclin E, cdc2, E2F, B-myb and DHFR (Zwicker J. and Müller R. (1997) Trends Genet. 13, 3-6).

Examples of regulable elements which permit metabolism-specific expression in eukaryotes are promoters which are regulated by hypoxia, by glucose deficiency, by phosphate concentration or by heat shock.

An example of a regulable element which permits keratinocyte-specific expression in skin is the FiRE element (Jaakkola et al., 2000, Gen. Ther., 7: 1640–1647). The FiRE element is an AP-1-driven, FGF-inducible response element of the syndecan-1 gene (Jaakkola et al., 1998, FASEB J., 12: 959–9).

Examples for regulable elements which allow spatial and temporal expression are nucleic acids coding for a fusion between the site specific recombinase Cre and a modified estrogen receptor. The expression of this fusion protein is controlled by a tissue specific promoter. The resulting cytoplasmic fusion protein can translocate into the nucleus upon administration of the estrogen analogue tamoxifen and induce recombination (Feil et al., 1996, Proc Natl Acad Sci 93: 10887–90).

In order to enable the nucleic acids which can be used in accordance with the invention to be introduced into a eukaryotic or prokaryotic cell by means of transfection, transformation or infection, and thereby enabling the polypeptide to be expressed, the nucleic acid can be present as a plasmid, or as a part of a viral or non-viral vector. Particularly suitable viral vectors in this context are: baculoviruses, vaccinia viruses, adenoviruses, adeno-associated viruses and herpesviruses. Particularly suitable non-viral vectors in this context are: liposomes, virosomes, cationic lipids and polylysine-conjugated DNA.

Examples of vectors which are applicable in gene therapy are viral vectors, for example adenoviral vectors or retroviral vectors (Lindemann et al., 1997, Mol. Med. 3: 466–76; Springer et al., 1998, Mol. Cell. 2: 549–58). Eukaryotic expression vectors are suitable for use in gene therapy when present in isolated form since naked DNA can penetrate into skin cells when applied topically (Hengge et al., 1996, J. Clin. Invest. 97: 2911–6; Yu et al., 1999, J. Invest. Dermatol. 112: 370–5).

Vectors which are applicable in gene therapy can also be obtained by complexing the nucleic acid which can be used in accordance with the invention with liposomes, since this makes it possible to achieve a very high efficiency of transfection, particularly of skin cells (Alexander and Akhurst, 1995, Hum. Mol. Genet. 4: 2279–85). In lipofection, small, unilamellar vesicles consisting of cationic lipids are prepared by subjecting the liposome suspension to ultrasonication. The DNA is bound ionically on the surface of the liposomes, specifically in a relationship which is such that a positive net charge remains and 100% of the plasmid DNA is complexed by the liposomes. In addition to the DOTMA (1,2-dioleoyloxypropyl-3-trimethylammonium bromide) and DPOE (dioleoylphosphatidylethanolamine) lipid mixtures employed by Felgner et al. (1987, see above), a large number of new lipid formulations have by now been synthesized and tested for their efficiency in the transfection of various cell lines (Behr, J. P. et al. (1989), Proc. Natl. Acad. Sci. USA 86, 6982–6986; Felgner J. H. et al. (1994) J. Biol. Chem. 269, 2550–2561; Gao, X. and Huang L. (1991), Biochim. Biophys. Acta 1189, 195–203). Examples of the new lipid formulations are DOTAP N-[1-(2,3-dioleoyloxy)propyl]-N,N,N-trimethylammonium ethyl sulfate or DOGS (TRANSFECTAM; dioctadecylamido-glycylspermine). The Cytofectin GS 2888 cationic lipids have also proved to be very well suited for transfecting keratinocytes in vitro and in vivo (U.S. Pat. No. 5,777,153; Lewis et al., 1996, Proc. Natl. Acad. Sci. USA, 93: 3176–3181). Auxiliary substances which increase the transfer of nucleic acids into the cell can, for example, be proteins or peptides which are bound to DNA or synthetic peptide-DNA molecules which make it possible to transport the nucleic acid into the nucleus of the cell (Schwartz et al. (1999) Gene Therapy 6, 282; Branden et al. (1999) Nature Biotech. 17, 784). Auxiliary substances also encompass molecules which enable nucleic acids to be released into the cytoplasm of the cell (Planck et al. (1994) J. Biol. Chem. 269, 12918; Kichler et al. (1997) Bioconj. Chem. 8, 213). Liposomes are a pharmaceutically acceptable carrier within the meaning of the present invention. Liposomes comprise multilamellar vesicles (MLVs), small unilamellar vesicles (SUVs) and large unilamellar vesicles (LUVs).

Methods for preparing liposome-nucleic acid complexes are known to the skilled person (e.g. Straubinger et al., 1983, in Methods of Immunology, 101: 512–527; Szoka et al., 1978, Proc. Natl. Acad. Sci. USA, 75: 4194–4198), The term "liposomes" encompasses, for example, liposomal compositions which are disclosed in U.S. Pat. No. 5,422,120, WO 95/13796, WO 94/23697, WO 91/14445 and EP 524,968 B1. Liposomes can be used for nucleic acids usable according to the invention as well as for polypeptides usable according to the invention or for both as a pharmaceutical carrier, preferably they are used as pharmaceutical carriers for the nucleic acids according to the invention. The therapeutically active substance can also be conjugated to the liposome or it can be conjugated to a hydrogel polymer, wherein the hydrogel polymer (or a component of the hydrogel polymer) is conjugated to a liposome or can be enclosed by a liposome. Another especially suitable form of gene therapeutical vectors can be obtained by applying the nucleic acid usable according to the invention to gold particles and apply these topically with the aid of the so called "gene gun" by shooting them into the skin or cells (Example 3; Wang et al., 1999, J. Invest. Dermatol., 112: 775–81, Tuting et al., 1998, J. Invest. Dermatol., 111: 183–8).

The term "liposomes" encompasses, for example, liposomal compositions which are disclosed in U.S. Pat. No. 5,422,120, WO 95/13796, WO 94/23697, WO 91/14445 and EP 524,968 B1. Liposomes can be used as a pharmaceutical carrier for the nucleic acids which can be used in accordance with the invention and the polypeptides which can be used in accordance with the invention; they are preferably used as a pharmaceutical carrier for the nucleic acids which can be used in accordance with the invention. The therapeutically active substance can be conjugated to the liposome or it can be conjugated to a hydrogel polymer, with it being possible for the hydrogel polymer (or a component of the hydrogel polymer) to be conjugated to a liposome or to be enclosed by a liposome. Another particularly preferred form of vector for gene therapy can be obtained by applying the nucleic acid which is used in accordance with the invention to gold particles and using a Gene Gun to administer the particles topically by shooting the loaded particles into the skin or cells (Example 3; Wang et al., 1999, J. Invest. Dermatol., 112: 775–81, Tuting et al., 1998, J. Invest. Dermatol, 111:

183-8). Devices for performing intradermal injection using pressure have been disclosed, for example, in U.S. Pat. No. 5,630,796.

Another form of vector which is applicable in gene therapy can be prepared by introducing "naked" expression vectors into a biocompatible matrix, for example a collagen matrix. This matrix can, for example, be introduced into diabetes-associated and/or arterial wounds in order to transfect the immigrating cells with the expression vector and to express the polypeptides used in accordance with the invention in the cells (Goldstein and Banadio, U.S. Pat. No. 5,962,427).

For the use of the previously described nucleic acid in gene therapy it is also advantageous if the part of the nucleic acid which encodes the polypeptide contains one or more non-coding sequences, including intron sequences, preferably between the promoter and the start codon for the polypeptide (see Example 3) and/or a polyA sequence, in particular the naturally occurring polyA sequence or an SV40 virus polyA sequence, in particular at the 3' end of the gene since this thereby makes it possible to stabilize the mRNA (Jackson, R. J. (1993) Cell 74, 9-14 and Palmiter, R. D. et al. (1991) Proc. Natl. Acad. Sci.USA 88, 478-482).

Cells can be either prokaryotic or eukaryotic cells. Examples of prokaryotic cells are *E. coli,* and examples of eukaryotic cells are *Saccharomyces cerevisiae* or insect cells. Thus, *E. coli* cells have, for example, proved to be suitable cells for expressing human ACT (Rubin et al., 1990, J. Biol. chem., 265: 1199-1207). The use of *E. coli* cells for preparing polypeptides which can be used in accordance with the invention constitutes a preferred embodiment. The polypeptides which can be used in accordance with the invention are prepared, for example, by expressing the previously described nucleic acid in a suitable expression system, as already described above, using methods which are well known to the skilled person. Examples of suitable cells are the *E. coli* strain DHS, HB101 or BL21, the yeast strain *Saccharomyces cerevisiae,* the insect cell line Lepidopteran, e.g. from *Spodoptera frugiperda,* or the animal cells COS, Vero, 293, HaCaT and HeLa, all of which are generally available.

Preference is given to the treatment and prevention of diabetic ulcer and/or arterial ulcer or of a poorly healing wound in a diabetic patient or of a poorly healing wound in a patient suffering from arteriosclerotic destruction of the blood vessels.

Another preferred embodiment of the invention is the use of the ACT polypeptides which can be used in accordance with the invention in the form of a fusion protein for prevention and/or treatment of diabetes-associated and/or arterial wounds which heal poorly, which fusion protein is prepared using a previously described nucleic acid which can be used in accordance with the invention.

This involves preparing fusion proteins which contain the above-described polypeptides which can be used in accordance with the invention or their functional variants, with the fusion proteins themselves already constituting a functional variant of one of the previously described ACT polypeptides or only being a functional variant after the fusion moiety has been eliminated. These fusion proteins include, in particular, fusion proteins which have a content of approx. 1-300, preferably approx. 1-200, particularly preferably approx. 1-150, in particular approx. 1-100, and especially approx. 1-50, foreign amino acids. Examples of such peptide sequences are prokaryotic peptide sequences which can be derived, for example, from *E. coli* galactosidase.

Other preferred examples of peptide sequences for fusion proteins are peptides which facilitate detection of the fusion protein; they include, for example, green fluorescent protein or variants thereof.

The polypeptides which can be used in accordance with the invention can also be prepared synthetically. Thus, the entire polypeptide, or parts thereof, can, for example, be synthesized by means of classical synthesis (Merrifield technique). Particular preference is given to using polypeptides which have been prepared recombinantly using one of the previously described nucleic acids. Furthermore, ACT polypeptides can be isolated from an organism or from tissue or cells and then used in accordance with the invention. Thus, it is possible, for example, to purify polypeptides which can be used in accordance with the invention from human serum, for example (Abdullah et al., 1983, Arch. Biochem, Biophys., 225:306-312). Furthermore, it is possible to prepare cell lines from ACT-expressing cells, which cell lines can then be used for isolating ACT. Thus, active ACT can, for example, be prepared by recombinant expression in *E. coli* cells (Rubin et al., 1990, J. Biol. Chem. 265: 1199-1207).

It is possible to add on at least one "polypeptide tag" for the purpose of purifying the previously described proteins. For example, suitable protein tags enable the proteins which are to be purified to be absorbed with high affinity to a matrix. This is then followed, for example, by the following steps: stringent washing with suitable buffers without eluting the complex to any significant extent, and, subsequently, specific elution of the absorbed complex. Examples of the protein tags which are known to the skilled person are a $(His)_6$ tag, an Myc tag, a FLAG tag, a hemagglutinin tag, a glutathione transferase (GST) tag, a tag consisting of a an intein flanked by an affinity chitin-binding domain, and a maltose-binding protein (MBP) tag. These protein tags can be located N-terminally, C-terminally and/or internally.

In another preferred embodiment, the antibody or antibody fragment useable according to the invention is a catalytic antibody which increases the activity of an ACT polypeptide according to the invention. Examples of catalytic antibodies are found for example in Tramontano et al., 1986, Science 234: 1566-70.

The present invention also relates to the use of an ACT polypeptide according to SEQ ID No. 1 to SEQ ID No. 4, or of a functional variant thereof, or of a nucleic acid encoding it, or a variant thereof, or of a cell which is expressing an ACT polypeptide according to SEQ ID No. 1 to SEQ ID No. 4, or a variant thereof, or a nucleic acid encoding it, or its variant, or a catalytic antibody according to the invention, where appropriate together or combined with suitable additives and auxiliary substances, for producing a pharmaceutical for treatment and/or prevention diseases which are selected from diabetes-associated wounds which heal poorly and/or arterial wounds which heal poorly.

The therapy of the diabetes-associated and/or arterial wounds which heal poorly can be effected in a conventional manner, e.g. using dressings, plasters, compresses or gels which contain the pharmaceuticals which can be used in accordance with the invention. Thus, it is possible to administer the pharmaceuticals topically and locally in order to exert an immediate and direct effect on wound healing. The topical administration of therapeutic compositions can be effected, for example, in the form of a solution, an emulsion, an cream, an ointment, a foam, an aerosol spray, a gel matrix, a sponge, drops or washings. Suitable additives or auxiliary substances are isotonic solutions, such as physiological sodium chloride solutions or sodium alginat, demineralized water, stabilizers, collagene containing substances such as Zyderm II or matrix-forming substances such as povidone. To generate a gel basis, formulations, such as aluminum hydroxide, polyacrylacid derivatives, such as Carbopol®, cellulose derivatives, such as carboxymethyl cellulose are suitable. These gels can be prepared as hydrogels on a water basis or as oleogels with low- and high molecular paraffines or vaseline and/or yellow or white wax. As emulsifier alkali soaps, metal soaps, amine soaps or partial fatty acid esters of sorbitants can be used whereas lipids can be added as vaseline, natural and synthetic waxes, fatty acids, mono-, di-, triglycerides, paraffin, natural oils, such as cocos oil, synthetic fats, such as Miglyol®. These forms of administration are preferred for using at least one ACT polypeptide which can be used in accordance with the invention. The pharmaceuticals according to the invention can also, where appropriate, be administered topically and locally, in the region of the wound, in the form of liposome complexes or gold particle complexes. This form of administration is preferred for vectors which are applicable in gene therapy and which contain a nucleic acid which can be used in accordance with the invention.

Furthermore, the treatment can be effected using a transdermal therapeutic system (TTS), which enables the pharmaceuticals according to the invention to be released in a temporally controlled manner. To improve the penetration of the administered drug through the membrane, additives such as ethanol, urea or propylene glycole can be added in addition to polymeric auxiliaries, such as Eudragit®. TTS have been disclosed, for example, in EP 0 944 398 A1, EP 0 916 336 A1, EP 0 889 723 A1 or EP 0 852 493 A1.

The pharmaceuticals according to the invention can also be administered as a cell, for example a keratinocyte, expressing a polypeptide of the invention which is then secreted to the wound site. A suitable carrier for administering those modified cells would be a micro carrier consisting of bio compatible materials, such as, for example a dextran matrix (U.S. Pat. No. 5,980,888).

However, the treatment with the pharmaceuticals according to the invention can also be effected systemically using parenteralia such as injections or infusions or peroralia. Injections can be applied subcutaneously, intradermally, intraepithelially, intrafusally, intramuscularly, intravenous, intracutaneously, intraperitoneally, or intrathecally and can be formulated as solutions, suspensions, as concentrates or lyophilized powder which can be diluted in isotonic solutions. Infusions can also be applied as isotonic solutions or as fat emulsions, as "high tech" formulations such as liposomes, micro emulsions, nanospheres, microspheres, microcapsules. To improve the adsorption of parenteral applied drugs to proteins or polymers and/or to reduce the association of the drug with glass or plastic surfaces, substances such as albumin, organic solvents, plasmaexpander or surface active substances could be used. Suitable auxiliaries for the production of parenteral applied drugs are isotonic substances, such as sodium chloride, isohydric substances, such as sodium hydrogen carbon acid or tensides or surface active substances and emulsifiers, such as Tween®, Cremophor®, or complex inducing substances such as urea and citrate. An alternative parenteral administration would be nasal, oral cavity or rectal administration. For nasal and oral cavity applications, administrations, such as a spray, an ointment, an aerosols or drops which can be inhaled could be used. Suitable propellants would be tetrahydrofluran or heptafluorpropan but manual pressure systems would also be suitable. These propellants could contain surface active substances such as isopropylmyristat. For the rectal administration clyster preparations, such as tablets or capsules or suppositories. As auxiliary substances, Witepsol®, Massa Estarium® or Novata® could be used. A modified form of parenteral release would be the usage of depots which are implanted under the skin which consist preferably on the basis of biological degradable polymers.

A further systemically applied form is the oral administration such as tablets, fizzy tablets, capsules, pellets, dragees, powder, granules, pastilles, chewing gum, drops or suspensions. Suitable auxiliaries are for example starch, lactose, talcum, stearine acid, cellulose, PVP or Aerosil®. Suitable additives are for example flavors, colors, antioxidants, vitamins, sweeteners, such as glucose or aspartam. These oral application systems can also be prepared as retard system by using, for example, Eudragit® or as gastrointestinal therapeutic system or oral osmotic system. The spatial liberation of the drug within the stomach or gut could be varied by the usage of coated tablets with different coats having different solubility.

Preference is given to pharmaceuticals which bring about an increase in the quantity and/or function, particularity the activity, of ACT polypeptides according to SEQ ID No. 1 to 4 or functional variants thereof. The polypeptides can be prepared synthetically or recombinantly or can be isolated from tissues or cells, with particular preference being given to preparation using an above-described expression system, in particular using *E. coli* cells. The recombinant proteins which have been prepared in this way can also be present as fusion proteins, e.g. so as to facilitate purification or detection.

Another preferred embodiment of a pharmaceutical according to the present invention is the administration of an activating antibody or fragments thereof which increases the activity of an ACT polypeptide, according to the present invention. The application of such a catalytic antibody can be performed as described above.

In another preferred embodiment, use is made of cells which contain at least one nucleic acid encoding an ACT polypeptide according to SEQ ID No. 1 to 4, or a functional variant thereof, for producing a pharmaceutical for treatment and/or prevention of diseases which are selected from diabetes-associated wounds which heal poorly and/or arterial wounds which heal poorly.

Particular preference is given to cells which can be used in accordance with the invention and which contain the nucleic acids in the form of an above-described expression vector or vector which is applicable in gene therapy. More preferred is the use of a cell expressing a fusion protein useable according to the invention, or an antibody or a fragment thereof useable according to the invention. The cells can then be introduced into the wound directly or, where appropriate, combined with suitable carrier systems and/or additives and/or auxiliary substances and then introduced into the wound. Suitable carrier systems have been disclosed, for example, in U.S. Pat. No. 5,980,888, WO 92/06179, EP 0242 270 or WO 90/02796. Preferred cells are autologous or allogenic cells, especially preferred are skin cells, in particular keratinocytes, endothelial cells and fibroblasts.

Particular preference is given to pharmaceuticals, for the gene therapy treatment, which comprise nucleic acids which can be used in accordance with the invention and which are contained in a vector or a cell, as explained above, or which comprise polypeptides which can be used in accordance with the invention.

Another preferred transformed cell, which can be used in accordance with the invention, is a transgenic, embryonic, non-human stem cell which is characterized by the fact that it comprises an expression cassette according to the invention. Methods for transforming cells and/or stem cells are well known to the skilled person and include, for example, electroporation and microinjection. The invention furthermore relates to the use of a transgenic, non-human mammal whose genome contains a previously-described expression cassette. In general, transgenic animals exhibit an elevated tissue-specific expression of the nucleic acids and/or polypeptides and are therefore suitable for preparing polypeptides which can be used in accordance with the invention. If, for example, a mammary gland-specific promoter is selected, the recombinant polypeptides which can be used in accordance with the invention can then be isolated from the milk which is produced (Clark, 1998, J. Mammary Gland Biol. Neoplasia, 3: 337–350). For example, expression of blood coagulation factor VIII in the mammary glands of transgenic sheep, under the control of the beta-lactoglobulin gene promoter, has been described (Niemann et al., 1999, Transgenic Res., 8: 237–247).

It is furthermore possible to use non-embryonic eukaryotic cells in a mammal in accordance with the invention by providing, for example by means of transfection, suitable cells or organs with an expression vector which contains the nucleic acids which can be used in accordance with the invention. Thus, using DEAE dextran or polyion complexes to transfect the guinea pig lactiferous duct with an expression vector containing the hGH gene results, for example, in continuous expression of hGH (Hens et al., Biochem. Biophys. Acta, 2000, 1523: 161–171).

Methods for preparing transgenic animals, particularly the mouse, are known to the skilled person, for example, from DE 196 25 049 and U.S. Pat. Nos. 4,736,866; 5,625,122; 5,698,765; 5,583,278 and 5,750,825 and comprise transgenic animals which can be generated, for example, by the direct injection of expression vectors (see above) into embryos or spermatocytes or by the transfection of expression vectors into embryonic stem cells (Polites and Pinkert: DNA Microinjection and Transgenic Animal Production, pages 15 to 68 in Pinkert, 1994: Transgenic Animal Technology: A Laboratory Handbook, Academic Press, London, UK: Houdebine, 1997, Harwood Academic Publishers, Amsterdam, The Netherlands; Doetschman: Gene Transfer in Embryonic Stem Cells, pages 115 to 146 in Pinkert, 1994, see above; Wood: Retrovirus-Mediated Gene Transfer, pages 147 to 176 in Pinkert, 1994, see above; Monastersky: Gene Transfer Technology; Alternative Techniques and Applications, pages 177 to 220 in Pinkert, 1994, see above).

The invention furthermore relates to the use of an ACT polypeptide according to SEQ ID No. 1 to SEQ ID No. 4, or a functional variant thereof, or of a nucleic acid encoding it, or of a cell which is expressing an ACT polypeptide according to SEQ ID No. 1 to SEQ ID No. 4, a functional variant thereof, or a nucleic acid encoding it, or an antibody or antibody fragment directed against a polypeptide according to SEQ ID No. 1 to SEQ ID No. 4, for preparing a diagnostic agent for diagnosis diseases which are selected from diabetes-associated wounds which heal poorly and/or arterial wounds which heal poorly. In this context, the diagnostic agent contains at least one antibody which is directed against a polypeptide which can be used in accordance with the invention or a functional variant thereof.

A diagnostic agent according to the present invention can be used to determine the expression level and/or function, particularly the activity level of a gene-of-interest within in a tissue sample to diagnose poorly healing, diabetes-associated and poorly healing arterial wounds. This method is especially preferred for early diagnosis of poorly healing diabetes-associated and poorly healing arterial wounds.

A preferred embodiment of a diagnostic agent is an antibody. Antibodies which can be used in accordance with the invention are known to the skilled person (e.g. EP 0162 812; EP 585201; Deininger et al., 1999, J. Neuroimmunol., 93: 156–63); however, they can also be prepared using well known methods: by immunizing a mammal, for example a rabbit, with the previously described ACT polypeptide or its functional variant, or parts thereof having a length of at least 6 amino acids, preferably of at least 8 amino acids, in particular of at least 12 amino acids, where appropriate in the presence of, e.g. Freund's Adjuvant and/or aluminum hydroxide gels (see, e.g. Diamond B. A. et al. (1981) The New England Journal of Medicine, 1344–1349). The polyclonal antibodies which are formed in the animal as the result of an immunological reaction can then readily be isolated from the blood using well-known methods and purified by column chromatography, for example. Monoclonal antibodies can be prepared, for example, using the known method of Winter & Milstein (Winter, G. & Milstein, C. (1991) Nature, 349, 293–299). According to the present invention, the term antibody is also understood as meaning recombinantly prepared, and modified, where appropriate, antibodies and antigen-binding parts thereof, such as chimeric antibodies, humanized antibodies, multifunctional antibodies, bispecific or oligo-specific antibodies, single-stranded antibodies and F(ab) or F(ab)2 fragments (see, e.g., EP-B1-0 368 684, U.S. Pat. Nos. 4,816,567, 4,816,397, WO 88/01649, WO 93/06213, WO 98/24884). Polyclonal rabbit anti-human antiserum is commercially available and could be used as diagnostic agent according to the present invention (Heidtmann et al., 1990, Clin Chem 36: 2077–2081). Using these antibodies, it is possible, for example, to investigate wound exudates readily and rapidly to determine whether an ACT polypeptide which can be used in accordance with the invention is or is not present in the wound exudates of an organism at a markedly higher quantity than it is in a normally healing wound. Alternatively, these antibodies can also be used to determine the function, particularly the activity, of an ACT polypeptide within wound exudates of an organism and compare the increase or decrease of activity to wound exudates derviving of normally healing wounds. Thus, it is possible to obtain an indication of a possible wound healing disturbance which can be treated according to the invention. For detecting the antibodies according to the invention, they are, for example, labeled with an enzyme, as has already been described. This makes it possible to detect the specific antibody-peptide complex readily, and just as rapidly, by way of an enzymatic color reaction (Example 3).

A further preferred embodiment of a diagnostic agent is a probe, preferably a DNA probe and/or a primer. For the preparation of a probe, a DNA- or RNA fragment with a length of approx. 100–1000 nucleotides, preferably with a length of 200–500 nucleotides, especially preferred with a length of 300–400 nucleotides are suitable. The sequence of these probes can be derived from a sequence according to the SEQ ID No. 5–8. These probes can be used, for example, for hybridization purposes, such as tissue sections or Northern blots.

Alternatively, primer sequences can be determined according to the sequences with the SEQ ID No. 5–8 which can be used in a PCR reaction. These primers can be used to amplify and isolate a nucleic acid, according to the present invention, or cDNA fragments thereof (Examples 1, 2, 3, 4).

As a suitable length for a primer, 10–100 nucleotides, preferable 15–50 nucleotides, extremely preferred 20–30 nucleotides are preferred.

The invention furthermore relates to the use of an ACT polypeptide according to SEQ ID No. 1 to SEQ ID No. 4 or of a nucleic acid encoding it, or of a cell which is expressing an ACT polypeptide according to SEQ ID No. 1 to SEQ ID No. 4 or a nucleic acid encoding it, or an antibody or antibody fragment directed against a polypeptide according to SEQ ID No. 1 to SEQ ID No. 4, for identifying pharmacologically active substances which exert an influence on the function, particularly on the activity, of ACT polypeptides.

In a preferred embodiment at least one ACT polypeptide according to SEQ ID No. 1 to SEQ ID No. 4, or a cell expressing the polypeptide or a nucleic acid coding for the polypeptide, or an antibody or a fragment thereof directed against the polypeptide, is bound to a solid phase and at least one substance is examined for its pharmacological activity in order to identify pharmacologically active substances which exert an influence on the function, particularly on the activity, of ACT polypeptides and mRNAs which are encoding them.

In another preferred embodiment at least one ACT polypeptide is expressed by at least one cell and at least one substance is examined for its pharmacological activity in order to identify pharmacologically active substances which exert an influence on the function, particularly on the activity, of ACT polypeptides and mRNAs which are encoding them.

For example, this can be effected by means of a system for testing the influence of potential pharmacologically active substances on the function, particularly on the activity, of ACT in the cells of the skin, in particular keratinocytes, monocytes, neutrophilic granulocytes, fibroblasts and endothelial cells.

In a preferred embodiment, at least one ACT polypeptide which can be used in accordance with the invention is expressed by at least one cell, and at least one substance is investigated for its pharmacological activity. For this, a cell culture can, for example, be brought into contact with liquid which contains a substance to be investigated. In order to determine an extracellular activity, the cells are separated from the supernatant, for example by means of centrifugation. The cell supernatant can then be isolated and examined for its ACT activity. In order to determine the intracellular ACT activity, the supernatant can be removed and the cells can be lysed. The cell lysate can then be examined for its ACT activity. In the case of ACT which possesses a signal peptide, both the intracellularly located and the extracellularly located ACT polypeptide can be tested for its activity. In the case of an ACT polypeptide which does not have a signal peptide, it is suitable to determine the activity of the intracellular ACT. Well-known protease inhibitor assays are suitable for determining the ACT activity (Chase and Shaw, 1967, Biochem. Biophys. Re. Commun., 29: 508–514), with it being possible to standardize against cathepsin G, for example (Example 5, Heidtmann et al., 1990, Clin Chem 36: 2077–2081, Kainulainen et al., 1998, 273: 11563–11569).

Another suitable test system which can be used in accordance with the invention is based on identifying interactions with the two hybrid system (Fields and Sternglanz, 1994, Trends in Genetics, 10, 286–292; Colas and Brent, 1998 TIBTECH, 16, 355–363). In this test system, cells are transformed with expression vectors which express fusion proteins which consist of at least one polypeptide according to the invention and a DNA-binding domain of a transcription factor such as Gal4 or LexA. The transformed cells also contain a reporter gene whose promoter contains binding sites for the corresponding DNA-binding domain. By means of transforming a further expression vector, which expresses a second fusion protein consisting of a known or unknown polypeptide and an activation domain, for example from Gal4 or herpes simplex virus VP16, the expression of the reporter gene can be greatly increased if the second fusion protein interacts with the investigated polypeptide according to the invention. This increase in expression can be used for identifying new interacting partners, for example by preparing a cDNA library from regenerating tissue for the purpose of constructing the second fusion protein. This test system can also be used for screening substances which inhibit an interaction between the polypeptide according to the invention and an interacting partner. Such substances decrease the expression of the reporter gene in cells which are expressing fusion proteins of the polypeptide according to the invention and the interacting partner (Vidal and Endoh, 1999, Trends in Biotechnology, 17: 374–81). In this way, it is possible to rapidly identify novel active compounds which can be employed for the therapy of and/or prevention of diabetes-associated and/or arterial poorly healing wounds.

In another preferred embodiment, at least one ACT polypeptide, or a nucleic acid coding for the polypeptide, or a cell expressing an ACT polypeptide or a nucleic acid coding for the polypeptide according to the invention, or an antibody or antibody fragment directed against a polypeptide according to SEQ ID No. 1 to SEQ ID No. 4, is bound to a solid phase and at least one substance is examined for its pharmacological activity. The binding to a solid phase can be effected, for example, in the form of an array. Methods for preparing such arrays using solid phase chemistry and photolabile protecting groups have been disclosed, for example, in U.S. Pat. No. 5,744,305. Suitable test systems for studying a pharmacological effect of test substances on an ACT protein which is bound to a solid phase are well known and include protease inhibitor assays (Chase and Shaw, 1967, Biochem. Biophys. Re. Commun., 29: 508–514), with it being possible for the standardization to be effected, for example, against cathepsin G (see Example 5, Heidtmann et al., 1990, Clin Chem 36: 2077–2081, Kainulainen et al., 1998, 273: 11563–11569). Test systems which are suitable for identifying substances which increase the activity of ACT and which have as little influence as possible on the activity of control proteins, such as GAPDH, are particularly to be preferred. Moreover, test systems for studying a pharmacological effect of test substances on a cell expressing a polypeptide or a polynucleotide according to the invention which is bound to a solid phase are well known. For example intracellular or extracellular ACT activity can be determined as described above (see also Example 5).

Furthermore, it is possible to examine, in a wound-healing assay, for example carried out on a mouse, whether the application of substances, either separately or together with ACT polypeptides and/or nucleic acids encoding them, to a wound alters the wound healing. This can be determined, for example, by measuring the rate of reepithelialization.

The invention furthermore relates to the use of an ACT polypeptide according to SEQ ID No. 1 to SEQ ID No. 4, or of a nucleic acid encoding it, or of a cell which is expressing an ACT polypeptide according to SEQ ID No. 1 to SEQ ID No. 4 or a nucleic acid encoding it, or an antibody or antibody fragment directed against a polypeptide according to SEQ ID No. 1 to SEQ ID No. 4, for identifying pharmacologically active substances which exert an influence on the expression of ACT polypeptides and mRNAs which are encoding them. Test systems for identifying pharmacological substances which exert an influence on the expression of genes are well known to the skilled person (see, for example, Sivaraja et al., 2001, U.S. Pat. No. 6,183,956).

In another preferred embodiment at least one ACT polypeptide according to the invention is expressed by at least one cell and at least one substance is examined for its pharmacological activity in order to identify pharmacologically active substances which exert an influence on the expression of ACT polypeptides and mRNAs which are encoding them.

Thus, cells which express ACT which can be used in accordance with the invention, for example neutrophiles, can be cultured as a test system for analyzing gene expression in vitro, with preference being given to skin cells, in particular keratinocytes, fibroblasts or endothelial cells. In this context, a possible test system is a human keratinocyte cell line HaCaT, which is generally available.

Gene expression is analyzed, for example, at the level of the mRNA or of the proteins. In this context, the quantity of ACT mRNA or protein is measured, after adding one or more substances to the cell culture, and compared with the corresponding quantity in a control culture. This takes place, for example, by means of the hybridization of an antisense probe, which can be used to detect the ACT mRNA which is present in the lysate of the cells. The hybridization can be quantified, for example, by binding a specific antibody to the mRNA-probe complex (see Stuart and Frank, 1998, U.S. Pat. No. 4,732,847). In this context, it is possible to carry out the analysis as a high-throughput method, for example, and to analyze a very large number of substances for their suitability for use as modulators of ACT expression (Sivaraja et al., 2001, U.S. Pat. No. 6,183,956).

The substances to be analyzed can be taken from substance libraries (see, e.g., DE 19816414 and DE 19619373) which can contain several thousand substances which are frequently very heterogeneous. Alternatively, the total RNA or mRNA can first of all be isolated from cells and the absolute quantity, or the relative proportion, of the ACT mRNA can then, for example, be determined by means of quantitative RT-PCR (see Example 1, 2, 4, EP 0 200 362; Wittwer et al., 1997, BioTechniques 22: 130–8; Morrison et al., 1998, BioTechniques 24: 954–62) or by means of an RNAse protection assay (see, e.g., Sambrook et al., 1989, Molecular cloning: A Laboratory Manual, Cold Spring Harbor, Cold Spring Harbor Laboratory Press, New York, chapter 7; EP 0 063 879). Another possibility is that of analyzing the quantity of protein in the cell lysate using antibodies which specifically recognize ACT polypeptides which can be used in accordance with the invention. In this case, the quantification can be effected, for example, using an ELISA or a Western blot, which are well known. In order to determine the specificity of the substances for the expression of ACT, the influence of substances on ACT expression can be compared with their influence on the expression of other genes, for example metabolism genes such as GAPDH. This can be done either in separate analyses or in parallel with the analysis of the ACT. Test systems which are suitable for identifying substances which increase the expression of ACT and which exert as little influence as possible on the expression of one or more control genes, such as GAPDH, are particularly to be preferred.

Another embodiment of the invention relates to the pharmacologically active substances which are identified using the screening method.

The invention furthermore relates to a pharmaceutical comprising pharmacologically active substances for treatment of poorly healing diabetes-associated wounds and poorly healing arterial wounds.

In a preferred embodiment, at least one ACT polypeptide which can be used in accordance with the invention is bound to a solid phase and at least one substance is examined for its pharmacological activity.

In another preferred embodiment, at least one ACT polypeptide which can be used in accordance with the invention is expressed by at least one cell and at least one substance is examined for its pharmacological activity.

In a particularly preferred embodiment of the invention, at least two substances are, for the purpose of identifying pharmacological substances, examined for their pharmacological activities, with the substances being selected from at least one library of substances.

The invention also relates to a process for producing a pharmaceutical, in which, in a first step, a pharmacologically active substance is identified using one of said methods for identifying such substances and, in a further step, the pharmacologically active substance(s) which has/have been identified is/are brought into contact, or combined, with suitable auxiliary substances and/or additives.

The invention will now be further clarified with the aid of the following tables, sequence listing submissions, and examples without it being restricted thereto.

Table 1: Tabular summary of the ACT polypeptides which can be used in accordance with the invention and cDNAs encoding them, and also their access numbers as found in the SwissProt, Genebank, and the indicated patent specification.

Table 2: Tabular summary of the relative expression of mACT in various mouse wound healing models. Experiments were carried out using young, old, poorly and normally healing Balb/c mice. Experiments performed with diabetic and the corresponding control animals were performed with C57/B1/Ks and C57/B1/Ks-db/db/Ola mice, respectively. To generate poorly healing wounds, mice of the Balb/c stain were treated with the drug dexamethasone (DEX).

Table 3: Mean values for the changes in the tensile strength of the wounds in normal and diabetic rats which were treated with mACT by means of gene therapy, relative to the tensile strength of wounds which were treated with a control vector. The E/C value is the quotient of the absolute tensile strength measured in a rat treated with ACT (E) and the absolute tensile strength measured in a rat treated with a control vector (C).

Table 4: Kinetic of the differential regulation of ACT expression in wound healing of normal and diabetic mice in relation to the time ((h)hours and (d)ays) after wounding relative to intact skin determined by means of “Taq-Man”-Analysis as an example of a wound healing disorder which is in context with the lack of ACT.

Table 5: Comparative data on the differential expression of ACT expression in two different wound healing states of human (normal wound healing, and diabetic ulcera) determined by “Taq-Man”-Analysis as an example for a wound healing disorder selectively occurring in diabetic patients caused by a lack of ACT. “Pools of patients 1–5” represent RNA pools or cDNA pools, respectively, which were generated from biopsies of 6 healthy persons taken either from intact skin or the indicated time points after wounding. “Pools of patients 6–8” represent RNA or cDNA pools, respectively, which were generated from biopsies of 6 diabetic patients taken either from intact skin, the wound edge or—ground of a diabetes-associated ulcer.

Table 6: Comparison of the relative amount of active ACT protein within human wound exudates between normally healing wounds and those deriving from different poorly healing wounds as indicated which is an example of a reduced activity selectively occurring in diabetic-associated poorly healing wounds.

SEQ ID No. 1 to SEQ ID No. 4 show the sequences of polypeptides which can be used in accordance with the invention.

SEQ ID No. 5 to SEQ ID No. 8 show the sequences of nucleic acids which can be used in accordance with the invention.

SEQ ID No. 9 to SEQ ID No. 18 show the sequences of oligonucleotides which were used for the examples.

EXAMPLES

Example 1

TaqMan Analysis of Murine ACT Expression in Normally Healing, Well Healing and 3 Different Types of Poorly Healing Wounds with Different Pathogenetic Backgrounds TaqMan analysis was used to determine, in a GeneAmp5700 supplied by Applied Biosystems, the strength of the expression of murine ACT (mACT) cDNAs, as first measured in various mouse wound healing models, thereby making it possible to correlate the pathogenetic background of the course of a wound healing with ACT expression. For this, normally healing day 1 wounds and intact skin were obtained from 10-week-old BALB/c mice, which had been treated with isotonic salt solution, by cutting with scissors. In order to obtain tissue from mice which exhibited particularly good wound healing, use was made of untreated day 1 wounds and intact skin which were obtained from 4-week-old, young BALB/c mice. Animals treated with the glucocorticoid dexamethasone (DEX animals), old animals and diabetic animals were used as animal models of poor wound healing (Davidson, 1998, Arch. Derm. Res., 290: S1–S11). In order to obtain DEX animals, BALB/c mice were treated with dexamethasone (0.5 mg of dexamethasone in isotonic salt solution per kg of bodyweight i.p. twice daily for 5 days) prior to wounding. Intact skin from mice which had been treated with isotonic salt solution, as described above, was used as the control. Tissue from old mice was isolated from untreated day 1 wounds and intact skin samples from 12-month-old BALB/c mice. Wound tissue and intact skin were obtained from diabetic mice (db/db mouse) by isolating untreated day 1 wounds and intact skin from 10-week-old C57B1/ks-db/db/Ola mice by cutting with scissors. C57B1/Ks wild-type mice were used as control animals in this context. Intact skin and untreated day 1 wounds were likewise obtained from the latter animals.

The RNA was isolated by homogenizing the biopsies in RNAclean buffer (AGS, Heidelberg) to which a 1/100 volume of 2-mercaptoethanol had been added using a dispenser. The RNA was then extracted by phenolizing it twice with water-saturated, acid phenol in the presence of 1-bromo-3-chloropropane. An isopropanol precipitation and an ethanol precipitation were then carried out and the RNA was washed with 75% ethanol. After that, the RNA was digested with DNase I. For this, 20 μg of RNA (made up to 50 μl with DEPC-treated water) were incubated, at 37° C. for 20 min, with 5.7 μl of transcription buffer (Roche), 1 μl of RNase inhibitor (Roche; 40 μl) and 1 μl of DNase I (Roche; 10 μl). A further 1 μl of DNase I was then added and the mixture was incubated at 37° C. for a further 20 min. The RNA was then phenolized, precipitated with ethanol and washed. All the above-listed steps were carried out using DEPC (diethyl pyrocarbonate)-treated solutions and/or liquids insofar as these solutions/liquids did not contain any reactive amino groups. The cDNA was then prepared from the extracted RNA. This was done in the presence of 1×TaqMan RT-buffer (Perkin Elmer), 5.5 mM $MgCl_2$ (Perkin Elmer), in each case 500 μM of dNTPs (Perkin Elmer), 2.5 μM random hexameres (Perkin Elmer), 1.25 U of MultiScribe Reverse Transcriptase/μl (50 U/μl Perkin Elmer), 0.4 U of RNase inhibitor/μl (20 U/μl, Perkin Elmer), 20 μl of RNA (50 ng/μl) and DEPC-treated water (to make up to a volume of 100 μl). After addition of the RNA, and after thorough mixing, the solution was aliquoted into 2×0.2 ml tubes (50 μl in each case) and the reverse transcription was carried out in a temperature cycler (10 min at 25° C.; 30 min at 48° C. and 5 min at 95° C.). The cDNA was subsequently quantified by quantitative PCR using the SYBR green PCR master mix (Perkin Elmer), with the mACT cDNA being determined in triplicate (in each case using mACT primers (mACT primer 3: 5' TCCAGTTGTGTCCCATTGTCA 3' (SEQ ID No. 13); mACT primer 4: 5' CTGTCCTCTGCTTCCCAGATG 3' (SEQ ID No. 14)); and GAPDH primers (GAPDH primers 1: 5' ATCAACGGGAAGCCCATC A 3' (SEQ ID No. 11); GADPH primer 2: 5' GACATACTCAGCACCGGCCT 3' (SEQ ID No. 12)). With a total volume of 57 μl, the stock solution for each triplet contained 37.5 μl of 2× SYBR master mix, 0.75 μl of AmpErase UNG (1 U/μl) and 18.75 μl of DEPC-treated water. For the determination in triplicate, 1.5 μl each of the forward and backward primers were added, in a previously optimized concentration ratio, to 57 μl of stock solution. In each case 60 μl of the stock solution/primer mixture were mixed with 15 μl of cDNA solution (2 ng/μl) and the whole was aliquoted into 3 reaction tubes. In parallel with this, a stock solution containing primers for determining GAPDH was prepared as the reference, mixed with a further 15 μl of the same cDNA solution and aliquoted into 3 reaction tubes. In addition, various cDNA solutions were prepared as a dilution series (4 ng/μl; 2 ng/μl; 1 ng/μl; 0.5 ng/μl and 0.25 ng/μl) for determining a standard curve for the GAPDH PCR. In each case, 15 μl of these cDNA solutions were mixed with 60 μl of stock solution/primer mixture for determining GAPDH and aliquoted into 3 reaction tubes. A standard curve was likewise constructed for the mACT PCR; the same dilutions were used for this as were used for the GAPDH standard curve. A PCR mixture without cDNA served as the control. 15 μl of DEPC water were in each case added to 60 μl of stock solution/primer mixture for mACT and for GAPDH and, after mixing, these solutions were in each case aliquoted into 3 reaction tubes. The mixtures were amplified in a GeneAmp 5700 (2 min at 50° C.; 10 min at 95° C., followed by 3 cycles of 15 s at 96° C. and 2 min at 60° C.; after that 37 cycles of 15 s at 95° C. and 1 min at 60° C.). The evaluation was effected by determining the relative abundance of mACT in relation to the GAPDH reference. For this, a standard curve was first of all determined by plotting the CT values of the dilution series against the logarithm of the quantity of cDNA in the PCR mixture (in ng of transcribed RNA) and the slope(s) of the straight line was determined. The efficiency (E) of the PCR is then given as follows: $E=10^{-1/s}-1$. The relative abundance (X) of the mACT cDNA (Y) in relation to GAPDH is then: $X=(1+E_{GAPDH})^{C_T(GAPDH)}/(1+E_Y)^{C_T(Y)}$. The numerical values were subsequently standardized by setting the quantity of cDNA from the intact skin of 10-week-old BALB/c animals, and the intact skin of the C57B1/Ks animals as respective control animals, equal to 1.

The relative changes in expression in the different wound healing models are compiled in Table 2. A marked increase in mACT expression to 5 to 13 times the quantity as compared with that in intact skin, was observed in day 1 wounds, both in the case of the animal models in which the wound healed normally and healed well and in the case of 2 animal models for disturbed wound healing, namely in the old animals and in the animals treated with glucocorticoid. Surprisingly, no significant differential regulation was observed in the wounds of the diabetic animals. This indicates that, disturbed wound healing is caused by a decreased expression of mACT and is specific for diabetes-associated wounds. The result of this experiment furthermore shows that mACT is surprisingly particularly effective, particularly for treatment and/or prevention of diabetes-associated and/or arterial wounds which heal poorly. In addition, the experiment shows, that ACT polynucleotides can be used in the diagnosis of diabetes-associated and/or arterial wounds which heal poorly.

Example 2

Kinetic of Expression of ACT During Wound Healing in Healthy and Diabetic Mice Determined by Means of "Taq-Man"-Analysis Since the successful closure of a wound is critically dependent on the fine tuned equilibrium of proteolytic and anti-proteolytic activity in the area of the wound during the entire healing process, kinetics of ACT expression during the wound healing process was compared in healthy and diabetic animals. To this end, punch-biopsies of wounds of intact skin were obtained from normal healing control mice (C57B1/6) and diabetic mice (C57B1/Ks-db/db/Ola) at different points in time (1 h, 7 h, 15 h, 24 h, 3 days, 5 day, 7 days, 14 days after wounding). The biopsies were homogenized and the RNA was isolated as described in Example 1. Subsequently, DNAse digestion and reverse transcription into cDNA was carried out. The quantification of wound healing relevant cDNAs was also carried out as described in Example 1. For the specific amplification of murine ACT primers according to SEQ ID No. 13 (5' TCCAGTTGT-GTCCCATTGTCA 3') and SEQ ID No. 14 (5' CTGTC-CTCTGCTTCCCAGATG 3') were selected based on the sequence of ACT (SEQ ID No. 5). GAPDH was used as a reference gene in this experiment. Therefore, primer according to SEQ ID No. 11 (5' ATCAACGGGAAGCCCATCA 3') and SEQ ID No. 12 (5' GACATACTCAGCACCGGCCT 3') were employed for PCR amplification based on the sequence of the GAPDH gene (Gene Bank: M17851). For the quantification in each reaction cDNA obtained from 10 ng reverse transcribed total-RNA was amplified in a total volume of 25 μl. The PCR was carried out according to the instructions of the manufacturer (PE Applied Biosystems, SYBR Green PCR and RT-PCR Reagents Protocol, 1998). The CT-Values were analyzed and the frequency of ACT mRNA relative to GAPDH mRNA was calculated based on these values (see Example 1). The results of the experiments are depicted in Table 4 and show that during the entire interval of observation ACT was expressed in a strongly reduced manner in diabetic animals relative to intact skin. The comparison with the expression kinetics observed in normally healing wounds disclose that within the first three days after wounding a strongly increased expression of the proteinase inhibitor ACT and thus a reduced activity of the corresponding protease seems indispensable for a normal wound healing process. This is evident from the extremely strongly increased expression of ACT during wound healing in healthy mice, which in the case of diabetic animals is reduced by a factor of 5.1.

These data demonstrate, that the differential expression is essential for the normal course of wound healing process over a long time span of the wound healing. This observation also represents an important criteria for establishing suitable time points for the therapy which would most preferably comprise the first days after wounding. Moreover, the comparison of the level of ACT expression in mice with normal wound healing and diabetic mice with a delayed wound healing unambiguously shows that a reduced expression of ACT leads to severe disorders of wound healing.

Example 3

Improving the Wound Healing in Diabetic Rats by Administering the Murine ACT Homologue in Vivo The aim now was to examine whether an increase in the quantity of mACT in rat wounds would in fact lead to improved wound healing in diabetic animals. For this, wound healing was investigated after administering the murine ACT gene, according to SEQ ID No. 1, to diabetic male Sprague Dawley rats. In order to quantify the wound healing, the tensile strength of the wounds was investigated, with a higher tensile strength reflecting an improvement in wound healing.

The diabetic rat animal model is an established model system for investigating diabetes-associated wounds which heal poorly (Davidson, Arch. Dermatol. Res. 290: S1–S11). Since diabetes is accompanied by microangiopathy, this animal model is also suitable for investigating arterially determined disturbances in wound healing.

A suitable expression vector, pMHint, which was prepared on the basis of the vector pMH (S. Hoffman-La Roche), was first of all constructed by inserting intron II of the rat insulin gene into the HindIII cleavage site between the CMV promoter and the multiple cloning site. The mACT cDNA was then cloned into pMHint using the multiple cloning site. For this, the coding region of the mACT cDNA according to SEQ ID No. 4 was amplified by PCR (mACT primer 1: 5'GAGGTACCATGGCTTTCATTGCAG 3'(SEQ ID No. 9) and mACT primer 2: 5'GAATCACGTGACCAC-CTCCTTTGGGGTTGG CTATC 3' (SEQ ID No. 10)), then cut with KpnI and Pm1I and ligated to the expression vector pMHint which had been cut with KpnI and Pm1I, thereby giving rise to the expression plasmid pMHintACT. pMHint which contained a luciferase gene (pMHIntLuc) was used as the control vector.

In order to induce the diabetes, 4 rats having a bodyweight of 250–300 g were injected i.p. with a freshly prepared aqueous solution of streptozotocin (Sigma) (50 mg/kg of bodyweight). The blood sugar of the animals was checked 7–9 days after induction, with a blood sugar level value of more than 200 mg/dL confirming the diabetic state.

The 4 diabetic rats and the 4 nondiabetic control animals were subsequently anaesthetized with a mixture consisting of 2% $O_2$ (2 l/min) and 1.25% isofluran. The back was depilated and 4 sites were marked on the back of each animal for subsequent wounding. In each case 0.5 μg of plasmid DNA immobilized on gold particles (BioRad) was fired into each site at 500 psi using a Helios gene gun (BioRad), with in each case 2 sites being bombarded with the ACT expression vector pMHIntACT and 2 sites being bombarded with the control vector pMHIntLuc and with in each case one bombardment with pMHIntACT being effected anteriorly and one bombardment being effected posteriorly. Incision wounds of 1 cm in length were then made through the bombarded sites and the wounds were closed with wound clips. The wound biopsies were taken after 10 days and the tensile strength of the wounds was determined using an Instron tensiometer in accordance with the manufacturer's instructions and standardized to the cross sectional area of the wounds. Subsequently, the quotient (E/C value) was calculated from the absolute value of the tensile strength of a wound which had been bombarded with pMHInt ACT and the absolute value of the tensile strength of a wound in the same animal which had been bombarded with the control vector pMHIntLuc. The mean of the E/C values was determined and the changes in tensile strength in dependence on mACT thereby ascertained. The means are given in Table 2.

It turned out that the tensile strength of the wounds treated with pMHIntACT was only clearly increased in the diabetic animals whereas the administration of this plasmid had no significant effect in the control animals. This highlights that the deregulation of expression of ACT in poorly healing, diabetes-associated and/or arterial poorly healing wounds can be specifically compensated for by administration of ACT and leads to a pronounced improvement of the wound healing. On the other hand, this treatment was not suitable for improving wound healing in the control animals, in which it was not possible to achieve any significant improvement in wound healing by administering mACT.

Example 4

Differential Expression of ACT mRNA in Human Biopsies of Intact Skin and Wounds of Healthy Subjects as Well as Biopsies of Diabetic Ulcera It was the object of this experiment to investigate to what extend the data of the animal experiments can be transferred to the human. To this end, the expression of human ACT was analyzed in different wound healing disorders: skin samples were obtained from normal intact skin, from wounds one hour after wounding, from day 1-wounds as well as day 5- and day 15-wounds were obtained by means of 4 mm and 6 mm punches from 6 patients and the biopsies of each point in time were pooled. In addition, punch-biopsies were taken at the same time from 6 patients with diabetic ulcera from intact skin as well as from the wound ground and the wound edge and subsequently the biopsies of each group (intact skin, wound base, wound edge) were pooled. The RNA was isolated from all the biopsies, digested with DNase-I, as described in Example 1. Then cDNA was synthesized using the extracted RNA (Example 1). The cDNA obtained in this way was quantified in three different reactions by means of quantitative PCR employing the SYBR Green PCR Master Mixes (Perkin Elmer) (see Example 1). To this end, the primer according to the SEQ ID No. 15 (5' AGGCCTTTGCCACTGACTTTC 3') and SEQ ID No. 16 (5' GCGAGTCAAGGTCCTTGATCA 3') were selected based on the SEQ ID No. 7 coding for human ACT. As a reference, instead of GAPDH Cyclophilin A (Gene Bank: XM039526) was employed which was amplified using the primers of the SEQ ID No. 17 (5' GGAATGGCAAGACCAGCAAG 3') and SEQ ID No. 18 (5' GGATACTGCGAGCAAATGGG 3'). The analysis was carried out by determining the relative abundance of ACT relative to the Cyclophilin A reference. Therefore, as shown in Example 1, first a standard curve was determined by plotting the CT values of the dilution series against the logarithm of the quantity of cDNA amount of the PCR reaction (in ng of transcribed RNA) and by determining the slope(s) of the straight line. The efficiency (E) of the PCR is then given as follows: $E=10^{-1/s}-1$. The relative abundance (X) of the ACT cDNA species (Y) analyzed in relation to Cyclophilin is then: $X=(1+E_{cyclophilin})^{C_T(cyclophilin)}/(1+E_y)^{C_T(Y)}$. The numerical values were subsequently standardized by setting the quantity of cDNA from the intact skin of healthy subjects equal to 1. The relative changes in the ACT expression in the different wound healing states is depicted in table 5. As a result, similar to the animal experiments a 3- to 7-fold increased ACT expression was observed in all wound healing states of healthy subjects analyzed relative to intact skin. In contrast, in patients suffering from diabetic poorly healing ulcera there was no increase of the amount of ACT at the wound edge corresponding to the normal values during the wound healing. In these patients the amount of ACT in the wound edge was only increased by a factor of 1.9 whereas in the wound ground essentially no expression of ACT was present. Therefore the protease/proteaseinhibitor-equilibrium is shifted in favor of the protease and thus to a deteriorated wound healing.

This experiment demonstrates that the differential expression of ACT during the wound healing process is also essential for the normal process of wound healing in human. Moreover this experiments unambiguously shows that the results of the animal experiments can be transferred to humans: in humans the deregulation of the level of expression of ACT according to the invention also depends on the pathogenetic background of the patient. Thus the poor wound healing in diabetic patients is caused by a reduced abundance of ACT which specifically occurs in this disease especially in the chronic region of the wound.

Example 5

Determination of ACT Activity in Human Wound Exudates of Normally Healing Wounds, Poorly Healing Venous Ulcers, and Wounds of Diabetic Patients This experiment was aimed to show by means of an activity assay for ACT that ACT polypeptides are inactive in poorly healing diabetic wounds. To this end, the activity of ACT polypeptides was measured in wound exudates from patients with different poorly healing wounds and compared to the activity found in wound exudates derived from acute normally healing wounds after surgery.

The measurement of activity of ACT polypeptides was performed by an activity assay according to Heidtmann et al., 1990, Clinical Chemistry 36: 2077-2081. The principle of this assay comprises the coating of a 96 well-microtiter plates with cathepsin G. Cathepsin G can bind active ACT molecules from wound exudates. After complexing active ACT polypeptides with cathepsin G, ACT polypeptides are detected by a primary rabbit anti-human antibody against ACT polypeptides, followed by a secondary goat anti-rabbit antibody which is coupled to alkaline phosphatase. The amount of bound, active ACT polypeptide is than detected by the application of a chromogenic substrate for alkaline phosphatase by monitoring the increase in absorbance 490 nm in a Versamax Plate reader (Molecular Devices).

To start this experiment, wound exudates from one patient suffering from a venous ulcer and wound exudates from wounds from 2 diabetic patients were collected for a period of 24 h and 48 h, respectively, as examples for poorly healing wounds. As a control, wound exudates from one acute normally healing patient were also collected for 24 h and 48 h, respectively. Those wounds typically arise in the course of surgeries aiming at a mamma reduction. The wound exudates from poorly healing wounds were collected by vaccum therapy: a vacuum extractor was applied to the corresponding wound together with a sponge which equally distributes the pressure on the wound. The aspirated fluid was collected by a bottle. In contrast, the wound exudates which derive from wounds after the acute surgical control wounds were collected by a drainage system which is located within the subcutaneous tissue of the wound and which usually applied to post-surgical wounds to prevent infections (Redon's suction drainage). Subsequently, collected wound exudates were centrifuged in 10 ml Falcon tubes at 1500 rpm at 4° C. in a Heraeus Multifuge 3 S-R for 10 min. to remove contaminating cells. The centrifugation was once repeated with the supernatant at 10000 rpm at 4° C. for 15 min to complete purification. Purified wound exudates from different patients were than diluted 1:5000, 1:10000, and 1:20000 in PBS-Tween to perform the activity assay. Therefore, 96 well-microtiter plates were first coated with 200 µl bovine serum albumin solution (10 g/l BSA in 50 mM NaHCO3, pH 9.6), covered with plate sealers (Qiagen) and incubated for 30 min. at 37° C. Afterwards, BSA solution was aspirated and microtiter plates were washed 4 times with 250 µl PBS for 2 min. The washing solution was then replaced by 100 µl coupling solution which was prepared by 1000 fold dilution of a stock solution (3.3 g/l cathepsin G (Calbiochem) in 50 mM sodium acetate, pH 5.5 and 0.5 M NaCl). Again the incubation period was 30 min. at 37° C. and wells were washed 4 times with 250 µl PBS-Tween for 2 min. To control the coupling of cathepsin G in general, 100 ill of a cathepsin G substrate solution (200 µg/l succinyl-alanyl-alanyl-proplyl-valyl-p-nitroanilide in 0.1 M 4-(2-hydroxyethyl)-1-piperazineethanesulfonate buffer, pH 7.5, 1 M NaCl, 12% DMSO) were added to the microtiter plate. After an incubation period at 37° C. for 100 min., the increase in absorbance at 414 nm was measured in a Versamex plate reader. To control the quantitive amount of cathepsin G coupled to the microtiter plate after the 30-min. incubation period the activity of cathepsin G in the coupling solution was compared with and without incubation in the microtiter plate. Therefore, 100 µl substrate solution (5 g/l succinyl-alanyl-alanyl-proplyl-valyl-p-nitroanilide in DMSO) were added to 900 µl of the coupling solution before and after contacing the microtiter plate. The increase in absorbance was messured for both solutions at 414 nm at 25° C. for 1 min. Results were within the linerarity of the assay.

Cathepsin G pre-bound microtiter plates were incubated with 100 µl diluted wound exudates from the acute normally healing wounds, wound exudates from the venous ulcer, wound exudates from wounds of the two diabetic patients, and as a control without addition of any wound exudates. Samples from all patients and all concentrations were applied to the microtiter plate in duplicate. The incubation period again took place at 37° C. with sealed microtiter plates for 30 min., followed by repeated washing with PBS-Tween. After the incubation period, microtiter plates were incubated with 100 µl rabbit anti-human ACT antibody (Dako; 1:1000 in PBS-Tween, 2.5% dry milk) at 37° C. for 30 min. and washed 4 times with PBS-Tween. Incubation of the primary antibody was followed by incubation with a 100 µl of a secondary goat anti-rabbit antibody which was coupled to alkaline phosphatase (Promega, 1:5000 in PBS-Tween, 2.5% dry milk) at 37° C. for 30 min., followed by the washing procedure as described above. As a negative control of the antibody, wells on the microtiter plate were prepared which contain either only wound exudates, only primary antibody, only secondary antibody, only wound exudates with primary antibody, only wound exudates with secondary antibody, or only PBS-Tween, respectively. Alkaline phosphatase was detected by incubation at room temperature with 100 µl/well of OPD (Dako; 6.6 mg/l containing 420 µl/l 30% $H_2O_2$). The reaction was stopped by adding 100 µl of 0.5M $H_2SO_4$ per well and absorbance was measured at 490 nm with the above-described ELSIA reader. In parallel, a calibration series was determined by diluting commercially available ACT (Calbiochem; 1 mg/ml in 20 mM Tris, pH 7.4 and 150 mM NaCl) stepwise. A standard curve was determined by plotting the dilution series (1:5000, 1:8000, 1:10000, 1:12000, 1:20000; 1:30000, 1:40000, 1:50000, 1:80000, 1:100000, and 1:120000) against the absorbance measured at 490 nm. Subsequently, the amount of active ACT polypeptides in the different wound exudates was determined by means of the standard curve.

The numerical values were than standardized by setting the mean value of the amount of active ACT polypeptides measured in the wound exudates collected for a period of 24 h from acute normally healing wounds equal to 1. The relative changes of the mean value of active ACT polypeptides measured in the wound exudates from the different patients after different collection periods are depicted in Table 6.

The results clearly show a 3.3- and 2.3-fold reduced amount of active ACT polypeptides in poorly healing wounds of diabetic patients compared to acute normally healing wounds. Moreover, the results demonstrate that the reduction of active ACT is essentially selective to poorly-healing, diabetes-associated wounds as the amount of active ACT in wound exudates of poorly healing venous ulcers is within the increasing range of acute normally healing wounds. Thus, the exceptional position of ACT among other antiserine-proteases and within the anti-protease shield theory is clearly established by this experiment as the shortness of ACT within diabetes-associated wounds is the reason for poor healing of this special type of poor healing wounds whereas other factors are responsible for the poor healing of other poorly healing wounds, such as venous ulcers, for example. Surprisingly, these experiments clearly demonstrate the result that ACT is very efficient in the prevention and/or treatment of diabetes-associated and/or arterial poorly healing wounds. The effect of ACT is specific for these wound healing disorders and is essentially not suited for the treatment of other wound healing disorders since there is no deregulation of the ACT expression and function, particularly activity, in the latter diseases (Examples 1, 2, 4, 5).

For prevention and/or treatment, the amount and/or the activity of ACT, has to be increased in the region of the wound. Indications which are preferably to be treated are diabetic ulcer and arterial ulcer, in particular diabetic ulcer. The administration of a pharmaceutical comprising ACT is preferably effected topically, preferably by means of gene therapy. The administration can furthermore preferably be effected by means of the topical application of a recombinant ACT polypeptide according to the invention, since the site of action of the ACT polypeptide is extracellular and it is consequently not necessary for the protein to penetrate into cells. A further preferred embodiment of a pharmaceutical comprises a substance which increases the function, in particular the activity of ACT polypeptides, for examplea catalytic antibody or a fragment thereof directed against an ACT polypeptide and activating the polypeptide.

In particular, the sequence variants depicted in SEQ ID No. 1, 2, 3 or 4 and/or their mature variants, with or without a partial signal peptide moiety, can be used for prevention and/or treatment.

It will be apparent to those skilled in the art that various modifications can be made to the compositions and processes of this invention. Thus, it is intended that the present invention cover such modifications and variations, provided they come within the scope of the appended claims and their equivalents.

Priority application DE 10121255.0 was filed Apr. 30, 2001 and the U.S. provisional application Ser. No. 60/323, 348 was filed Sep. 18, 2001. All publications cited herein are incorporated in their entireties by reference.

TABLE 1

| Name | Organism | Protein SEQ ID No. | Access number Protein | cDNA SEQ ID No. | Access No. cDNA |
|---|---|---|---|---|---|
| 1. mACT | *Mus musculus* | 1 | — | 5 | — |
| 2. SERINE PROTEASE INHIBITOR 2-2 | *Mus musculus* | 2 | trEMBL: Q62258 | 6 | Genbank: M64086 |
| 3. alpha-1-antichymotrypsin | *Homo sapiens* | 3 | — | 7 | — |
| 4. 4 AA + mature alpha-1-antichymotrypsin | *Homo sapiens* | 4 | US5367064-A; FIG. 1 | 8 | US5367064-A; FIG. 1 |

TABLE 2

| Tissue sample | Relative quantity of mACT |
|---|---|
| Intact skin, Balb/c control animals | 1.0 |
| Wound, Balb/c control animals | 13.3 |
| Intact skin, Balb/c young animals | 0.6 |
| Wound, Balb/c young animals | 5.6 |
| Intact skin, Balb/c DEX animals | 0.8 |
| Wound, Balb/c DEX animals | 7.7 |
| Intact skin, Balb/c old animals | 0.5 |
| Wound, Balb/c old animals | 5.2 |
| Intact skin, C57B1/Ks control animals | 1.0 |
| Wound, C57B1/Ks control animals | 5.4 |
| Intact skin, C57B1/ks-db/db/Ola diabetic animals | 4.4 |
| Wound, C57B1/ks-db/db/Ola diabetic animals | 4.0 |

TABLE 3

| Mean E/C values | |
|---|---|
| Control animals | Diabetic animals |
| 1.142 | 3.397 |

TABLE 4

| Time after wounding of mice | Relative expression of ACT mRNA in C57B1/6 mice | Relative expression of ACT mRNA in C57B1/Ks-db/db/Ola mice |
|---|---|---|
| intact skin | 1.0 | 1.0 |
| 1 h | 0.4 | 0.3 |
| 7 h | 7.2 | 0.8 |
| 15 h | 8.6 | 1.4 |
| 24 h | 8.6 | 2.2 |
| 3 d | 8.1 | 1.4 |
| 5 d | 2.0 | 0.8 |
| 7 d | 2.5 | 0.5 |
| 10 d | 2.0 | 0.3 |
| 14 d | 2.0 | 0.5 |

TABLE 5

| Biopsy | Relative amount of ACT cDNA |
|---|---|
| pool of patients 1: intact skin healthy patients | 1.00 |
| pool of patients 2: 1 h-wound healthy patients | 2.77 |
| pool of patients 3: day 1-wound healthy patients | 7.66 |
| pool of patients 4: day 5-wound healthy patients | 7.00 |

TABLE 5-continued

| Biopsy | Relative amount of ACT cDNA |
|---|---|
| pool of patients 5: day 15-wound healthy patients | 3.00 |
| pool of patients 6: intact skin patients with diabetic ulcera | 1.00 |
| pool of patients 7: wound edge patients with diabetic ulcera | 1.86 |
| pool of patients 8: wound base patients with diabetic ulcera | 0.00 |

TABLE 6

| Source of human wound exudate | Time Period of wound exudate collection | Relative amount of active ACT protein |
|---|---|---|
| Surgical wound after mamma reduction | 24 h | 1 |
| Surgical wound after mamma reduction | 48 h | 1.6 |
| venous ulcer | 24 h | 1.4 |
| venous ulcer | 48 h | 1.2 |
| chronic wound of diabetic patients | 24 h | 0.3 |
| chronic wound of diabetic patient | 48 h | 0.7 |

The invention claimed is:

1. A method of diagnosing a disorder selected from the group consisting of poorly healing diabetes-associated wounds and poorly healing arterial wounds, in a patient, the method comprising determining, in a wound sample from the patient, the level of a nucleic acid encoding a polypeptide having the sequence of SEQ ID NO: 3, wherein a level of the nucleic acid in the wound sample from the patient that is lower than the level in a control sample indicates that said patient has the disorder.

2. The method of diagnosing according to claim 1, wherein the wounds are a diabetic ulcer or an arterial ulcer.

3. The method of diagnosing according to claim 1, wherein the level of the nucleic acid is determined using a DNA or RNA probe.

4. The method of diagnosing according to claim 1, wherein the level of the nucleic acid is determined using a DNA or RNA primer is a DNA.

* * * * *